United States Patent [19]
Will

[11] Patent Number: 6,001,611
[45] Date of Patent: Dec. 14, 1999

[54] MODIFIED NUCLEIC ACID AMPLIFICATION PRIMERS

[75] Inventor: Stephen Gordon Will, Walnut Creek, Calif.

[73] Assignee: Roche Molecular Systems, Inc., Pleasanton, Calif.

[21] Appl. No.: 09/039,866

[22] Filed: Mar. 16, 1998

Related U.S. Application Data

[60] Provisional application No. 60/041,127, Mar. 20, 1997.

[51] Int. Cl.$^6$ .............................. C12P 19/34; C12Q 1/68; C07H 21/04; C07H 21/00
[52] U.S. Cl. ........................... 435/91.2; 435/6; 536/23.1; 536/24.3; 536/24.33; 536/25.3; 536/25.32; 536/26.71
[58] Field of Search ..................... 435/6, 91.2; 536/23.1, 536/24.3, 24.33, 25.3, 25.31, 25.32, 26.71

[56] References Cited

U.S. PATENT DOCUMENTS

| | | | |
|---|---|---|---|
| 5,256,549 | 10/1993 | Urdea et al. | 435/91 |
| 5,459,255 | 10/1995 | Cook et al. | 536/27.13 |
| 5,476,928 | 12/1995 | Ward et al. | 536/24.3 |
| 5,576,427 | 11/1996 | Cook et al. | 536/23.1 |

OTHER PUBLICATIONS

Sinha et al., 1993, Biochimie 75: 13–23.

Griffin and Reese, 1963, "The Synthesis of $N^1$ and $N^6$–Methyladenosine 5'–Pyrophosphates Possible Substrates for Polynucleotide Phosphorylase" *Biochim. Biophys. Acta* 68: 185–192.

Reardon et al., 1990, "DNA Polymerase Action on Bulky Deoxyguanosine and Deoxyadenosine Adducts" *Carcinogenesis* 11 (1): 165–168.

Misra et al., Aug., 1992, "Chemical and Enzymatic Incorporation of $N^2$(–p–n–butylphenyl)–2'–deoxyguanosine into an oligodeoxyribonucleotide" *Nucleic Acids Research* 20 (17): 4547–4551.

Sinha et al., 1993, *Biochimie* 75: 13–23.

Metzker et al., Jul., 1994, "Termination of DNA synthesis by Novel 3'–modified–deoxyribonucleoside 5'–triphosphates" *Nucleic Acids Research* 22 (20): 4259–4267.

Aritomo et al., Mar., 1995, "Alkylation of 6–N–acylated Adenosine Derivatives by the use of Phase Transfer Catalysis" *J.Chem. Soc. Perkin Trans. 1*: 1837–1844.

Gniazdowski and Cera, 1996, "The Effects of DNA Covalent Adducts on in vitro Transcription" *Chem. Rev.* 96: 619–634.

*Primary Examiner*—John L. LeGuyader
*Assistant Examiner*—Mark L. Shibuya
*Attorney, Agent, or Firm*—Douglas A. Petry

[57] ABSTRACT

The present invention provides modified primers for use in the amplification of a nucleic acid sequence. Amplifications carried out using the modified primers result in less non-specific amplification product, in particular, primer dimer, and a concomitant greater yield of the intended amplification product compared to amplifications carried out using unmodified primers.

22 Claims, 6 Drawing Sheets

U = unmodified ST778AA/ST280A
B = bis-nitrobenzyl 15239/15240
M = mononitrobenzyl 15241/15242

M = Molecular weight marker
A = Amplifications with KY18/KY75
B = Amplifications with benzyl-KY436/benzyl-KY75
C = Amplifications with *p-tert*-butylbenzyl-KY436/*p-tert*-butylbenzyl-KY75

Synthesis of derivatized dA CPG

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
       (A) LENGTH: 33 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:1:

CAATGAGACA CCAGGAATTA GATATCAGTA CAA                          33

(2) INFORMATION FOR SEQ ID NO:2:

(i) SEQUENCE CHARACTERISTICS:
       (A) LENGTH: 32 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:2:

CCCTAAATCA GATCCTACAT ATAAGTCATC CA                           32

(2) INFORMATION FOR SEQ ID NO:3:

(i) SEQUENCE CHARACTERISTICS:
       (A) LENGTH: 26 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:3:

GCAGAAAGCG TCTAGCCATG GCGTTA                                   26

(2) INFORMATION FOR SEQ ID NO:4:

(i) SEQUENCE CHARACTERISTICS:
       (A) LENGTH: 28 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:4:

GCAAGCACCC TATCAGGCAG TACCACAA                               28

(2) INFORMATION FOR SEQ ID NO:5:

(i) SEQUENCE CHARACTERISTICS:
       (A) LENGTH: 23 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:5:

```
CACATGCAAG TCGAACGGAA AGG                                                    23

(2) INFORMATION FOR SEQ ID NO:6:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

TAACACATGC AAGTCGAACG GAAA                                                   24

(2) INFORMATION FOR SEQ ID NO:7:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

GCCCGTATCG CCCGCACGCT CACA                                                   24
```

MODIFIED NUCLEIC ACID AMPLIFICATION PRIMERS

This application claims priority to U.S. Provisional Application Serial No. 60/041,127, filed Mar. 20, 1997.

BACKGROUND OF THE INVENTION

1. Field of the Invention

The present invention relates to the field of molecular biology and nucleic acid chemistry. More specifically, it relates to methods and reagents for improving the yield of nucleic acid amplification reactions. The invention, therefore, has applications in any field in which nucleic acid amplification is used.

2. Description of Related Art

The invention of the polymerase chain reaction (PCR) made possible the in vitro amplification of nucleic acid sequences. PCR is described in U.S. Pat. Nos. 4,683,195; 4,683,202; and 4,965,188; Saiki et al., 1985, Science 230:1350–1354; Mullis et al., 1986, Cold Springs Harbor Symp. Quant. Biol. 51:263–273; and Mullis and Faloona, 1987, Methods Enzymol. 155:335–350; each of which is incorporated herein by reference. The development and application of PCR are described extensively in the literature. For example, a range of PCR-related topics are discussed in PCR Technology—principles and applications for DNA amplification, 1989, (ed. H. A.Erlich) Stockton Press, New York; PCR Protocols: A guide to methods and applications, 1990, (ed. M. A. Innis et al.) Academic Press, San Diego; and PCR Strategies, 1995, (ed. M. A. Innis et al.) Academic Press, San Diego; each of which is incorporated herein by reference. Commercial vendors, such as Perkin Elmer (Norwalk, Conn.), market PCR reagents and publish PCR protocols.

Since the original publication of nucleic acid amplification, various primer-based nucleic acid amplification methods have been described including, but are not limited to, Ligase Chain Reaction (LCR, Wu and Wallace, 1989, Genomics 4:560–569 and Barany, 1991, Proc. Natl. Acad. Sci. USA 88:189–193); Polymerase Ligase Chain Reaction (Barany, 1991, PCR Methods and Applic. 1:5–16); Gap-LCR (PCT Patent Publication No. WO 90/01069); Repair Chain Reaction (European Patent Publication No. 439,182 A2), 3SR (Kwoh et al., 1989, Proc. Natl. Acad. Sci. USA 86:1173–1177; Guatelli et al., 1990, Proc. Natl. Acad. Sci. USA 87:1874–1878; PCT Patent Publication No. WO 92/0880A), and NASBA (U.S. Pat. No. 5,130,238). All of the above references are incorporated herein by reference. A survey of amplification systems is provided in Abramson and Myers, 1993, Current Opinion in Biotechnology 4:41–47, incorporated herein by reference.

Specificity of primer-based amplification reactions depends on the specificity of primer hybridization. Under the elevated temperatures used in a typical amplification, the primers hybridize only to the intended target sequence. However, amplification reaction mixtures are typically assembled at room temperature, well below the temperature needed to insure primer hybridization specificity. Under such less stringent conditions, the primers may bind non-specifically to other only partially complementary nucleic acid sequences or to other primers and initiate the synthesis of undesired extension products, which can be amplified along with the target sequence. Amplification of non-specific primer extension products can compete with amplification of the desired target sequences and can significantly decrease the efficiency of the amplification of the desired sequence.

One frequently observed type of non-specific amplification product is a template independent artifact of amplification reactions referred to as "primer dimer". Primer dimer is a double-stranded fragment whose length typically is close to the sum of the two primer lengths and appears of occur when one primer is extended over the other primer. The resulting concatenation forms an undesired template which, because of its short length, is amplified efficiently.

Non-specific amplification can be reduced by reducing the formation of primer extension products prior to the start of the reaction. In one method, referred to as a "hot-start" protocol, one or more critical reagents are withheld from the reaction mixture until the temperature is raised sufficiently to provide the necessary hybridization specificity. In this manner, the reaction mixture cannot support primer extension during the time that the reaction conditions do not insure specific primer hybridization.

Manual hot-start methods, in which the reaction tubes are opened after the initial high temperature incubation step and the missing reagents are added, are labor intensive and increase the risk of contamination of the reaction mixture. Alternatively, a heat sensitive material, such as wax, can be used to separate or sequester reaction components, as described in U.S. Pat. No. 5,411,876, incorporated herein by reference, and Chou et al., 1992, Nucl. Acids Res. 20(7):1717–1723, incorporated herein by reference. In these methods, a high temperature pre-reaction incubation melts the heat sensitive material, thereby allowing the reagents to mix.

Another method of reducing the formation of primer extension products prior to the start of the reaction relies on the heat-reversible inhibition of the DNA polymerase by DNA polymerase-specific antibodies, as described in U.S. Pat. No. 5,338,671, incorporated herein by reference. The antibodies are incubated with the DNA polymerase in a buffer at room temperature prior to the assembly of the reaction mixture in order to allow formation of the antibody-DNA polymerase complex. Antibody inhibition of DNA polymerase activity is inactivated by a high temperature pre-reaction incubation. A disadvantage of this method is that the production of antibodies specific to the DNA polymerase is expensive and time-consuming, especially in large quantities. Furthermore, the addition of antibodies to a reaction mixture may require redesign of the amplification reaction.

The formation of extension products prior to the start of the reaction can also be inhibited by the addition to the reaction of a single-stranded binding protein, which non-covalently binds to the primers in a heat-reversible manner and inhibits primer extension by preventing hyridization.

Non-specific amplification also can be reduced by enzymatically degrading extension products formed prior to the start of the reaction using the methods described in U.S. Pat. No. 5,418,149, which is incorporated herein by reference. The degradation of newly-synthesized extension products is achieved by incorporating into the reaction mixture dUTP and UNG, and incubating the reaction mixture at 45–60° C. prior to carrying out the amplification reaction. Primer extension results in the formation of uracil-containing DNA, which is degraded by UNG under the pre-amplification conditions. A disadvantage of this method is that the degradation of extension product competes with the formation of extension product and the elimination of non-specific primer extension product is likely to be less complete. An advantage of this method is that uracil-containing DNA introduced into the reaction mixture as a contamination from a previous reaction is also degraded and, thus, the method also reduces the problem of contamination of a PCR by the amplified nucleic acid from previous reactions.

Conventional techniques of molecular biology and nucleic acid chemistry, which are within the skill of the art, are fully explained fully in the literature. See, for example, Sambrook et al., 1989, Molecular Cloning—A Laboratory Manual, Cold Spring Harbor Laboratory, Cold Spring Harbor, New York; Oligonucleotide Synthesis (M. J. Gait, ed., 1984); Nucleic Acid Hybridization (B. D. Hames and S. J. Higgins. eds., 1984); and a series, Methods in Enzymology (Academic Press, Inc.), all of which are incorporated herein by reference. All patents, patent applications, and publications mentioned herein, both supra and infra, are incorporated herein by reference.

SUMMARY OF THE INVENTION

The present invention provides covalently modified oligonucleotide primers for the in vitro amplification of nucleic acid sequences. Use of the modified primers of the invention results in a reduction in non-specific amplification, especially primer dinner formation, and/or a concomitant increase in the yield of the intended target relative to an amplification carried out with unmodified primers.

A variety of modifier moeities are envisioned which possess the following properties:

1. interfere with, but not prevent, Watson-Crick base pairing of the modified base with the complementary base;
2. interfere with, but not prevent, extension of the modified primer; and
3. allow synthesis of a strand complementary to the extension product of the modified primer.

One aspect of the invention relates to an oligonucleotide primer for the amplification of a nucleic acid sequence, having the general structure:

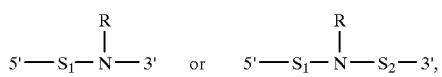

wherein $S_1$ represents a first sequence of nucleotides between about 5 and about 50 nucleotides in length;

wherein $S_2$ represents a second sequence between one and three nucleotides in length;

wherein N represents a nucleotide that which contains a purine or pyrimidine base that contains an exocyclic amine;

wherein R represents a modifier group, wherein R is covalently bound to N through the exocyclic amine, and and wherein R has the structure:

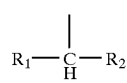

wherein $R_1$ and $R_2$ represent independently hydrogen, a $C_1$–$C_{10}$ alkyl group, an alkoxy group, a phenyl group, a phenoxy group, a substituted phenyl group, a napthyl group, or a substituted napthyl group. Alkyl groups may be branched or unbranched.

In a preferred embodiment, N is a modified conventional nucleotide, in which case N is a modified adenosine, cytidine, or guanosine, and the modifier moiety is covalently attached to the exocyclic amine of an adenine, guanine, or cytosine base. In a more preferred embodiment, N is a modified adenosine.

In a preferred embodiment, R is a 2-napthylmethyl group; a benzyl group; or a substituted benzyl group. Preferred substituted benzyl groups have the structure:

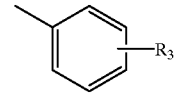

wherein $R_3$ represent a $C_1$–$C_6$ branched or unbranched alkyl group, more preferably a $C_1$–$C_4$ branched or unbranched alkyl group, a methoxy group, or a nitro group. Preferably, $R_3$ is attached in the para position.

In more preferred embodiment, R is a benzyl, p-methylbenzyl, p-tert-butylbenzyl, p-methoxybenzyl, or 2-napthylmethyl group.

Another aspect of the invention relates to amplification primers which are modified by the photo-labile covalent attachment of a modifier group, which results in a partial or complete inhibition of primer extension. The photo-labile modifier may be bound either to the exocyclic amine, as in the modified nucleotides described above, or to the ring nitrogen. In one embodiment, at least one nitrobenzyl group is attached to the exocyclic amine of an adenine, guanine, or cytosine base of the 3' terminal nucleotide.

Another aspect of the invention is a pair or set of primers, wherein at least one of the primers is modified as described above. In a prefered embodiment, both members of a pair, or all members of a set, of primers are modified.

Another aspect of the invention relates to methods for amplifying nucleic acid which comprise carrying out an amplificaton reaction using the modified primers of the invention.

Another aspect of the invention relates to methods for amplifying a target nucleic acid which comprise carrying out an amplificaton reaction using the photo-labile modified primers of the invention, wherein the reaction mixture is irradiated with light sufficient to remove the modifier group and allow formation of primer extension products. In one embodiment of the invention, the irradiation is carried out as a separate step, prior to the start of the amplification reaction, but after the reaction mixture has been heated to a temperature greater than about 50° C. In other embodiments, the irradiation step is combined with a preliminary step of the amplification process, such as the reverse transcription step of in an RNA amplification reaction, or the initial denaturation step in a DNA amplification reaction.

Another aspect of the invention relates to kits for the in vitro amplification of nucleic acid sequences, which kits comprise a pair of primers in which at least one of the primers is modified as described herein. The kits of the present invention also can include one or more amplification reagents, e.g., a nucleic acid polymerase or ligase, nucleoside triphosphatase, and suitable buffers.

DETAILED DESCRIPTION OF THE INVENTION

Figure 1:
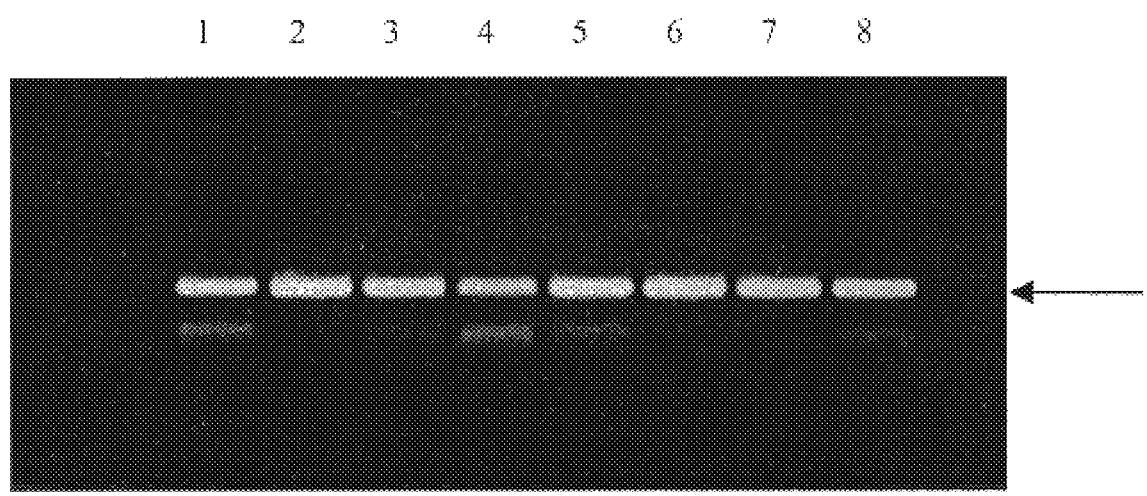
FIG. 1 shows the results of amplifications of HIV-1 RNA carried out using benzylated primers, as described in Example 5.

To aid in understanding the invention, several terms are defined below.

The terms "nucleic acid" and "oligonucleotide" refer to polydeoxyribonucleotides (containing 2-deoxy-D-ribose), to polyribonucleotides (containing D-ribose), and to any other type of polynucleotide which is an N glycoside of a purine or pyrimidine base, or modified purine or pyrimidine base. There is no intended distinction in length between the terms "nucleic acid" and "oligonucleotide", and these terms will be used interchangeably. These terms refer only to the primary structure of the molecule. Thus, these terms include double- and single-stranded DNA, as well as double- and single-stranded RNA.

The term "conventional", in reference to nucleic acid bases, nucleosides, or nucleotides, refers to those which occur naturally in the polynucleotide being described. The four conventional (also referred to as major) deoxyribonucleotides of DNA contain the purine bases adenine and guanine and the pyrimidine bases cytosine and thymine. The four conventional ribonucleotides of RNA contain the purine bases adendine and guanine and the pyrimidine bases cytosine and uracil. In addition to the above conventional or common bases, a number of other puring and pyrimidine derivatives, called rare or minor bases, occur in small amounts in some nucleic acids. As used herein, "unconventional", in reference to nucleic acid bases, nucleosides, or nucleotides, refers to rare or minor nucleic acid bases, nucleosides, or nucleotides, and modifications, derivations, or analogs of conventional bases, nucleosides, or nucleotides, and includes synthetic nucleotides having modified base moieties and/or modified sugar moieties (see, Protocols for Oligonucleotide Conjugates, Methods in Molecular Biology, Vol 26, (Sudhir Agrawal, Ed., Humana Press, Totowa, N.J., (1994)); and Oligonucleotides and Analogues, A Practical Approach (Fritz Eckstein, Ed., IRL Press, Oxford University Press, Oxford); both incorporated herein by reference).

Oligonucleotides can be prepared by any suitable method, including, for example, cloning and restriction of appropriate sequences and direct chemical synthesis by a method such as the phosphotriester method of Narang et al., 1979, *Meth. Enzymol.* 68:90–99; the phosphodiester method of Brown et al., 1979, *Meth. Enzymol.* 68:109–151; the diethylphosphoramidite method of Beaucage et al., 1981, *Tetrahedron Lett.* 22:1859–1862; and the solid support method of U.S. Pat. No. 4,458,066, each incorporated herein by reference. A review of synthesis methods is provided in Goodchild, 1990, *Bioconiugate Chemistry* 1(3):165–187, incorporated herein by reference.

The term "base pairing", also referred to in the art as "Watson-Crick base pairing", refers to the well known hydrogen bonding of complementary base pairs adenine-thymine and guanine-cytosine in a double stranded DNA structure, adenine-uracil and guanine-cytosine in a RNA/DNA hybrid molecule, and to analogous bonding of unconventional nucleotide pairs.

The term "hybridization" refers the formation of a duplex structure by two single-stranded nucleic acids due to complementary base pairing. Hybridization can occur between fully complementary nucleic acid strands or between "substantially complementary" nucleic acid strands that contain minor regions of mismatch. Conditions under which only fully complementary nucleic acid strands will hybridize are referred to as "stringent hybridization conditions" or "sequence-specific hybridization conditions". Stable duplexes of substantially complementary sequences can be achieved under less stringent hybridization conditions; the degree of mismatch tolerated can be controlled by suitable adjustment of the hybridization conditions. Those skilled in the art of nucleic acid technology can determine duplex stability empirically considering a number of variables including, for example, the length and base pair concentration of the oligonucleotides, ionic strength, and incidence of mismatched base pairs, following the guidance provided by the art (see, e.g., Sambrook et al., 1989, *Molecular Cloning—A Laboratory Manual*, Cold Spring Harbor Laboratory, Cold Spring Harbor, N.Y.; and Wetmur, 1991, Critical Review in Biochem. and Mol. Biol. 26(3/4) :227–259; both incorporated herein by reference).

The term "primer" refers to an oligonucleotide capable of acting as a point of initiation of DNA synthesis under conditions in which synthesis of a primer extension product complementary to a nucleic acid strand is induced, i.e., either in the presence of four different nucleoside triphosphates and an agent for extension (e.g., a DNA polymerase or reverse transcriptase) in an appropriate buffer and at a suitable temperature. As used herein, the term "primer" is intended to encompass the oligonucleotides used in ligation-mediated amplification processes, in which one oligonucleotide is "extended" by ligation to a second oligonucleotide which hybridizes at an adjacent position. Thus, the term "primer extension", as used herein, refers to both the polymerization of individual nucleoside triphosphates using the primer as a point of initiation of DNA synthesis and to the ligation of two primers to form an extended product.

A primer is preferably a single-stranded DNA. The appropriate length of a primer depends on the intended use of the primer but typically ranges from 6 to 50 nucleotides. Short primer molecules generally require cooler temperatures to form sufficiently stable hybrid complexes with the template. A primer need not reflect the exact sequence of the template nucleic acid, but must be sufficiently complementary to hybridize with the template. The design of suitable primers for the amplification of a given target sequence is well known in the art and described in the literature cited herein.

Primers can incorporate additional features which allow for the detection or immobilization of the primer but do not alter the basic property of the primer, that of acting as a point of initiation of DNA synthesis. For example, primers may contain an additional nucleic acid sequence at the 5' end which does not hybridize to the target nucleic acid, but which facilitates cloning of the amplified product. The region of the primer which is sufficiently complementary to the template to hybridize is refered to herein as the hybridizing region.

The terms "target, "target sequence", "target region", and "target nucleic acid" refer to a region or subsequence of a nucleic acid which is to be amplified.

As used herein, a primer is "specific" for a target sequence if the number of mismatches present between the primer sequence and the target sequence is less than the number of mismatches present between the primer sequence and non-target sequences which may be present in the sample. Hybridization conditions can be chosen under which stable duplexes are formed only if the number of mismatches present is no more than the number of mismatches present between the primer sequence and the target sequence. Under such conditions, the primer can form a stable duplex only with a target sequence. Thus, the use of target-specific primers under suitably stringent amplification conditions enables the specific amplification of those target sequences which contain the target primer binding sites. The use of sequence-specific amplification conditions enables the specific amplification of those target sequences which contain the exactly complementary primer binding sites.

The term "non-specific amplification" refers to the amplification of nucleic acid sequences other than the target sequence which results from primers hybridizing to sequences other than the target sequence and then serving as a substrate for primer extension. The hybridization of a primer to a non-target sequence is referred to as "non-specific hybridization" and can occur during the lower temperature, reduced stringency, pre-amplification conditions.

The term "primer dimer" refers to template-independent non-specific amplification product which results from primer extensions wherein another primer serves as a template. Although primer dimer frequently appears to be a concatamer of two primers, i.e., a dimer, concatamers of more than two primers also occur. The term "primer dimer" is used generically herein to encompasses template-independent non-specific amplification product.

The term "reaction mixture" refers to a solution containing reagents necessary to carry out a given reaction. An "amplification reaction mixture", which refers to a solution containing reagents necessary to carry out an amplification reaction, typically contains oligonucleotide primers and a DNA polymerase or ligase in a suitable buffer. A "PCR reaction mixture" typically contains oligonucleotide primers, a thermostable DNA polymerase, dNTP's, and a divalent metal cation in a suitable buffer. A reaction mixture is referred to as complete if it contains all reagents necessary to enable the reaction, and incomplete if it contains only a subset of the necessary reagents. It will be understood by one of skill in the art that reaction components are routinely stored as separate solutions, each containing a subset of the total components, for reasons of convenience, storage stability, or to allow for application-dependent adjustment of the component concentrations, and, that reaction components are combined prior to the reaction to create a complete reaction mixture. Furthermore, it will be understood by one of skill in the art that reaction components are packaged separately for commercialization and that useful commercial kits may contain any subset of the reaction components which includes the modified primers of the invention.

All patents, patent applications, and publications mentioned herein, both supra and infra, are incorporated herein by reference.

Modified Primers

The amplification primers of the invention are modified by the covalent attachment of a group to one of the four nucleotides at the 3'-terminal end of the primer. In one embodiment, a modified primer of the invention consists of a nucleic acid sequence having the general structure:

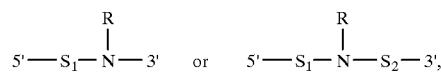

wherein $S_1$ represents a first sequence of nucleotides between about 5 and about 50 nucleotides in length;

wherein $S_2$ represents a second sequence between one and three nucleotides in length;

wherein N represents a nucleotide that which contains a purine or pyrimidine base that contains an exocyclic amine;

wherein R represents a modifier group, wherein R is covalently bound to N through the exocyclic amine, and wherein R has the structure described below.

As shown in the examples, the effect of the modification is maximized when the modification is to the 3' terminal nucleotide. Thus, preferably, the primer contains a modified 3' terminal nucleotide.

The modified nucleotide is selected from those whose base contains an exocyclic amine that is involved in the base pairing of the nucleotide with its complementary nucleotide. Typically, primers are DNA containing only conventional nucleotides. Of the four conventional nucleotide bases found in DNA, adenine, guanine, and cytosine contain an exocyclic primary amine which is involved in base pairing with the complementary base. In the preferred aspect of the invention, the primer is modified by the attachment of a single modifier group to the exocyclic amine, substituting for one of the two hydrogen of the amine group which, in the unmodified base, are capable of being involved in base pairing. The structures of the modified nucleotides containing a modified adenine, guanine, and cytosine base, respectively, are shown below.

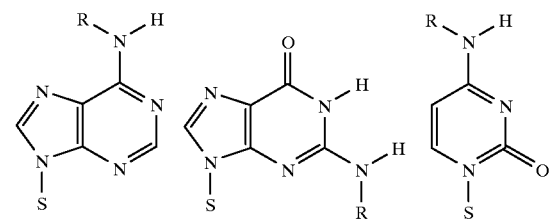

where S represents the sugar, and R represents the modifier group.

The present invention is not limited to primers consisting of conventional nucleotides. Any nucleotide analog in which the base moiety contains an exocyclic primary amine which is involved in base pairing with a complementary base is modifiable as described herein. Examples of unconventional nucleotides include 3-methyladenine, 7-methylguanine, 3-methylguanine, 5-methyl cytosine, and 5-hydroxymethyl cytosine.

The modifier group limits the ability of the modified base to participate in hydrogen bonding because the modifier substitutes for one hydrogen atom. The remining hydrogen atom still can participate in hydrogen bonding. The modifiers can therefore influence both the kinetics and thermodynamics of hybridization. A variety of modifier groups are envisioned which possess the following properties:

1. interfere with, but not prevent, Watson-Crick base pairing of the modified base with the complementary base;

2. interfere with, but not prevent, extension of the modified primer; and 3. allow synthesis of a strand complementary to the extension product of the modified primer.

The modifier group sterically interferes with base pairing and, thus, with primer extension. Thus, the physical bulk of the modifier influences the degree of interference with hybridization. When a modified adenosine or cytidine nucleotide is incorporated into a double-stranded nucleic acid, the modifier group protrudes into the central space of the major groove. Consequently, even relatively large modifier groups should cause little steric perturbation of the duplex structure. However, suitable modifiers are not so large such that hydrogen bonding is prevented or enzymatic extension of the 3'-hydroxyl of the primer is prevented. When the modified guanosine nucleotide is incorporated into a double-stranded nucleic acid, the modifier group protrudes into the minor groove, which provides less room to accomodate the bulk of the modifier group. Consequently, smaller modifier groups are prefered for attachment to a guanine base.

Primer extension products, which are used as templates in subsequent amplification cycles, contain the modified base introduced by the primer. The modifier group is chosen such that the presence of the modified base in the template does not cause termination of primer extension or inhibition of primer extension. Preferrably, the nature of the modifier group should not give rise to mutagenic events whereby the identity of the modified base is lost on replication of a primer-derived template. The effect of the modified base in the template on primer extension can be routinely tested following the guidance provided herein and in the art (see, for example, Gniazdowski and Cera, 1996, Chem. Rev. 96:619–634, incorporated herein by reference).

Modifier groups, R, which satisfy the above properties are suitable for use in the methods of the present invention. Prefered modifier groups have the structure:

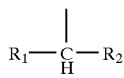

wherein $R_1$ and $R_2$ represent independently hydrogen, a $C_1$–$C_{10}$ alkyl group, an alkoxy group, a phenyl group, a phenoxy group, a substituted phenyl group, a napthyl group, or a substituted napthyl group. Alkyl groups may be branched or unbranched. Larger alkyl groups, up to at least $C_{20}$, may also be used.

In a preferred embodiment, R is a 2-napthylmethyl group; a benzyl group; or a substituted benzyl group. Preferred substituted benzyl groups have the structure:

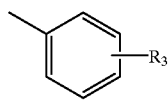

wherein $R_3$ represent a $C_1$–$C_6$ branched or unbranched alkyl group, more preferably a $C_1$–$C_4$ branched or unbranched alkyl group, a methoxy group, or a nitro group. Preferably, $R_3$ is attached in the para position.

Particularly preferred modifier groups are shown below:

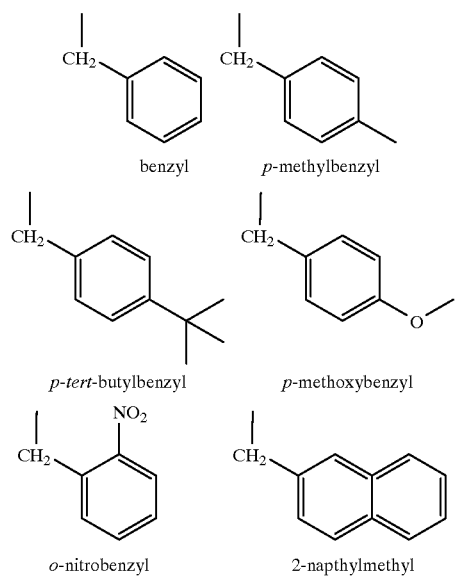

A number of particular modifier groups are described in the examples. In general, empirical selection of a particular suitiable modifier group from the class of compounds described can be carried out routinely by one of skill in the art following the guidance provided herein. Preferably, suitability of a particular group is determined empirically by using the modified primers in an amplification reaction. Successful amplification indicates both that the modified base does not totally inhibit primer extension, and that presence of the modified base in a primer derived template does not cause termination of primer extension. The reduction of primer dimer is determined as described in the examples.

Theory of operation

In each cycle of a primer-based amplification, primers are annealed to target nucleic acid, and the primers are enzymatically extended. The process is repeated typically between 25 and 40 times. The specificity of the amplification depends on the specificity of the primer hybridization step. Primer sequences and reaction conditions are selected such that the primers form stable hybridization duplexes only with the complementary sequences present in the intended target nucleic acid sequence.

It is believed that non-specific amplification occurs when an unstable, transient hybridization duplex is formed between a primer and a non-target molecule, possibly another primer, in which the 3' end of the primer is momentarily paired with a complementary base in the other molecule. Initial primer extension results in the formation of complementary sequence which stabilizes the duplex and allows further extension.

While not being constrained by the theory, it is believed that the stable modified primers of the present invention, which remain modified throughout the reaction, reduce non-specific amplification by increasing the time required for the initial primer extension to occur. The modifier group, when rotated towards the complementary base, sterically hinders base pairing. However, rotation of the amine into a configuration in which the hydrogen is directed towards the complementary base permits normal base pairing. Primer extension, which depends on the formation of matching base pairs at the 3' end of the primer, is delayed until the amine group has rotated into a permissive position and base pairing has occurred. The additional time required for the rotation into a permissive configuration reduces the likelihood that an unstable, transient hybridization duplex, such as between primers under pre-reaction conditions, will exist for a sufficient time to permit primer extension.

In contrast, primer-target hybridization duplexes are sufficiently stable under the primer hybridization condition used in an amplification so as to provide time for the rotation of the amine into a configuration which allows base pairing with the complementary base. Following hybridization, primer extension appears not to be affected. Thus, the modification does not significantly inhibit primer extension under the amplification conditions, but does decrease the probability of extension of primers involved in unstable, transient duplexes formed with non-target sequences under the pre-amplification conditions.

Primers with a Photo-labile Modification

In an alternative embodiment of the invention, primers are modified with one or more photo-labile groups which can be removed by exposure to light after the reaction has reach the high-temperature reaction conditions which insure specificity. Becauses the modifier is removed prior to primer extension, the modified primer need not be extendable prior to removal of the group. Examples of photolabile modifiers which can be used in the methods of the present invention are described in Pillai, 1980, "Photoremovable Protecting Groups in Organic Synthesis", Synthesis: 1–26, incorporated herein by reference.

Preferably, the photo-labile primers of the invention are modified at the 3' terminal nucleotide by the attachment of one or two o-nitrobenzyl groups:

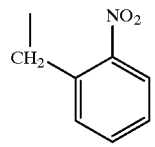

In primers modified by the attachment of a single nitrobenzyl group to the exocyclic primary amine of a base moiety, the resulting secondary amine still can participate in base pairing if the amine group is rotated such that the remaining hydrogen is oriented towards the complementary base. As described in the examples, these primers can be used in an amplification either with or without removal by irradiation with UV light.

Primers modified by the attachment of a two nitrobenzyl groups to the exocyclic amine of the base cannot be extended. The inhibition presumably results from the inability of the modified base to undergo base pairing, which is precluded because both hydrogens of the exocyclic amine are replaced by bulky nitrobenzyl groups. The use of primers modified with two nitrobenzyl groups in an amplification, in which the reaction mixture was exposed to UV light for a time sufficient to remove the nitrobenzyl groups, thereby allowing primer extension to take place, is described in the examples.

In an alternative embodiment, the modifier group is attached to the ring nitrogen. Primers modified by the attachment of a nitrobenzyl group to the ring nitrogen of the base cannot be extended due to the inability of the modified base to undergo base pairing. Removal of the nitrobenzyl groups by exposure to UV light allows primer extension to take place.

Use of the photo-labile primers which cannot be extended until the modifier group is removed essentially provides a "hot-start" amplification. Primer extension is inhibited during the non-specific pre-reaction conditions. The reaction is irradiated and the primers deblocked only after the reaction temperature has been raised to a temperature which insures reaction specificity.

Synthesis of Modified Primers

Synthesis of the modified primers is carried out using standard chemical means well known in the art. Methods for the introduction of these modifiers can be divided into four classes.

1. The modifier can be introduced by use of a modified nucleoside as a DNA synthesis support.
2. The modifier can be introduced by use of a modified nucleoside as a phosphoramidite.
3. The modifier can be introduced by the use of a reagent during DNA synthesis. (e.g., benzylamine treatment of a convertible amidite when incorporated into a DNA sequence).
4. Post-synthetic modification. The modifier can be introduced as a reactive reagent when contacted with synthetic DNA.

The synthesis of particular modified primers is described in the examples. Additional modified primers can be synthesized using standard synthesis methods in an analogous manner.

Figure 6:
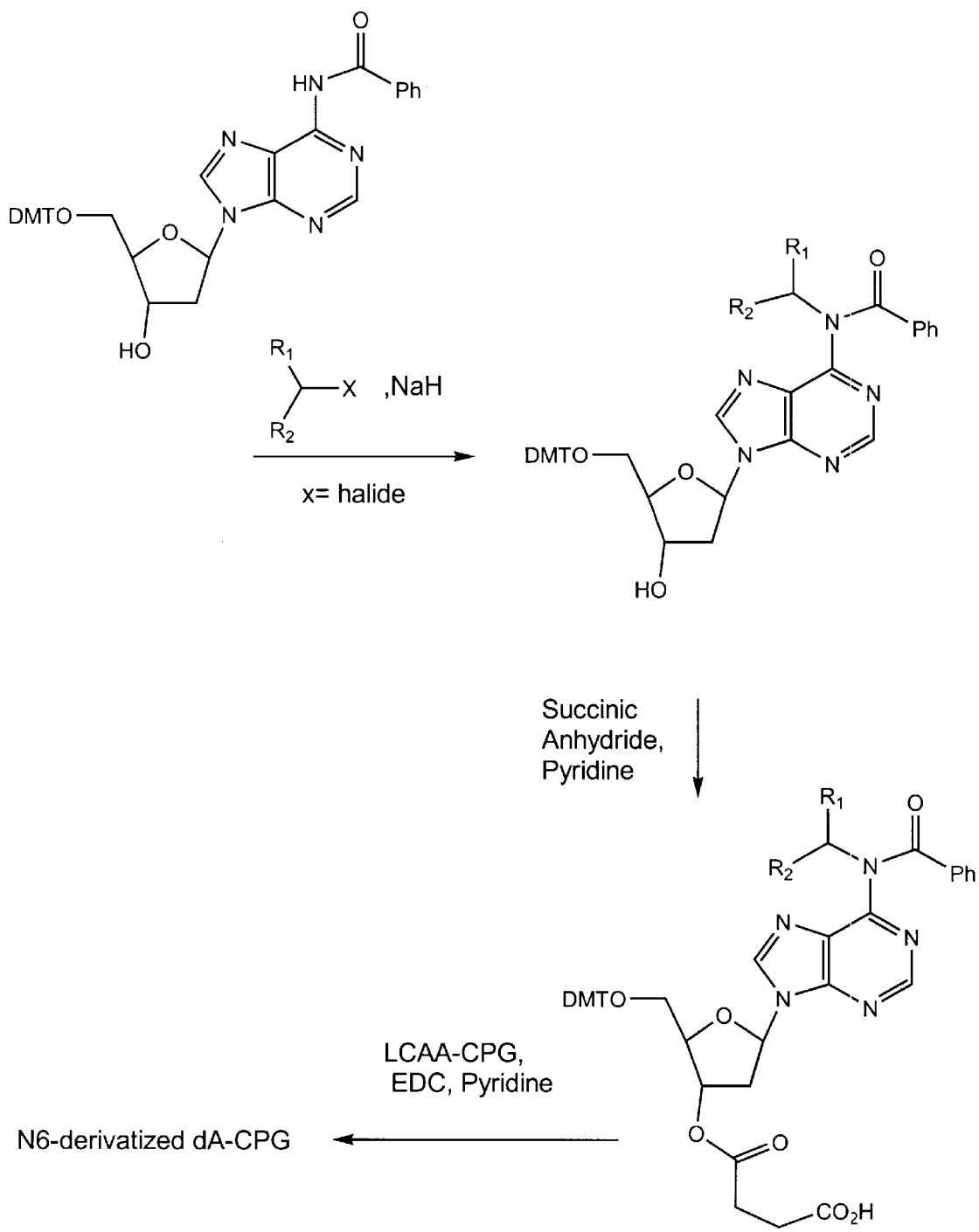
FIG. 6 shows a general reaction scheme suitiable for the synthesis of benzyl- or substituted benzyl-modified dA controlled pore glass (CPG).

Preferably, modified primers are synthesized using a derivatized controlled pore glass (CPG) synthesis support. A general reaction scheme for the synthesis of derivatized dA CPG is shown in FIG. 6. Particular modifier groups can be added by use of the appropriate alkyl-halide, benzyl-halide, substituted benzyl halide, methylnapthyl-halide, or substituted methylnapthyl-halide alkylating agent. The syntheses of the benzyl- and p-ert-butylbenzyl-dA CPG describes in Examples 1 and 2 follow the scheme shown in FIG. 6.

Alkylation of the exocyclic amino group can be carried out using methods analogous to the methylation described in Griffin and Reese, 1963, *Biochim. Acta* 68:185–192, incorporated herein by reference. Additional synthesis methods are described in Aritoma el al. 1995, J. Chem. Soc. Perkin Trans. 1: 1837–1844, which is incorporated herein by reference.

Amplifications using Modified Primers

The methods of the present invention comprise carrying out a primer-based amplification using the modified primers of the present invention. In general, the modified primers can be substituted for unmodified primers containing the same nucleotide sequence in a primer-based amplification with no change in the amplification reaction conditions. Of course, one of skill in the art will recognize that routine minor re-optimization of the reaction conditions may be benificial in some reactions.

In a preferred embodiment, the modified primers of the present invention are used in the polymerase chain reaction (PCR). However, the invention is not restricted to any particular amplification system. The modified primers of the present invention can be used in any primer-based amplification system in which primer dimer or non-specific amplification product can be formed. Examples include the amplification methods described in the references cited above. As other systems are developed, those systems may benefit by practice of this invention.

The methods of the present invention are suitable for the amplification of either DNA or RNA. For example, the amplification of RNA using a reverse transcription/polymerase chain reaction (RT-PCR) is well known in the art and described in U.S. Pat. Nos. 5,322,770 and 5,310,652, Myers and Gelfand, 1991, *Biochemistry* 30(31):7661–7666, Young et al., 1993, *J. Clin. Microbiol.* 31(4):882–886, and Mulder et al., 1994, *J. Clin. Microbiol.* 32(2):292–300, each incorporated herein by reference.

In a primer-based amplification, primer extension is carried out typically at an elevated temperature using a thermostable enzyme such as a thermostable DNA polymerase. The enzyme initiates synthesis at the 3' end of the primer and proceeds in the direction towards the 5' end of the template until synthesis terminates. Purified thermostable DNA polymerases useful in amplification reactions are well known in the art and include, but are not limited to, the enzymes described in U.S. Pat. No. 4,889,818; U.S. Pat. No. 5,079,352; U.S. Pat. No. 5,352,600; U.S. Pat. No. 5,491,086; WO 91/09950; WO 92/03556, WO 92/06200; WO 92/06202; WO 92/09689; and U.S. Pat. No. 5,210,036; each incorporated herein by reference. A review of thermostable DNA polymerases is provided in Abramson, 1995, in PCR Strategies, (ed. M. A. Innis et al.), pp 39–57, Academic Press, San Diego, incorporated herein by reference.

In a preferred embodiment, particularly for the amplification of DNA, the amplification is carried out using a reversibly inactivated enzyme as described in copending U.S. patent application Ser. Nos. 08/680,283 and 08/684,108, which both represent regular U.S. filings of provisional application No. 60/002,673, each incorporated herein by reference. The use of a reversibly inactivated enzyme, which is re-activated under the high temperature reaction conditions, further reduces non-specific amplification by inhibiting primer extension prior to the start of the reaction. A reversibly inactivated thermostable DNA polymerase, developed and manufactured by Hoffmann-La Roche (Nutley, N.J.) and marketed by Perkin Elmer (Norwalk, Conn.), is described in Birch et al., 1996, Nature 381(6581):445–446, incorporated herein by reference.

The effect of the modifier group on the ability of the enzyme to extend the primer depends, in part, on the particular enzyme used and, in part, on the reaction conditions selected. For example, Tth DNA polymerase is more permissive when $Mn^{2+}$ is used as the divalent cation, as in some RNA amplifications, rather that $Mg^{2+}$. One of skill will recognize that in the routine selection of a suitable modifier group, the enzyme and reaction conditions will be considered.

Sample preparation methods suitable for amplification reactions are well known in the art and fully described in the literature cited herein. The particular method used is not a critical part of the present invention. One of skill in the art can optimize reaction conditions for use with the known sample preparation methods.

Methods of analyzing amplified nucleic acid are well known in the art and fully described in the literature cited herein. The particular method used is not a critical part of the present invention. One of skill in the art can select a suitable analysis method depending on the application.

A preferred method for analyzing an amplification reaction is by monitoring the increase in the total amount of double-stranded DNA in the reaction mixture, as described in in Higuchi et al., 1992, *Bio/Technology* 10:413–417; Higuchi et al., 1993, *Bio/Technology* 11:1026–1030; European Patent Publication No. 512,334; and copending U.S. patent application Ser. No. 08/266,061; each incorporated herein by reference. In this method, referred to herein as "kinetic PCR", the detection of double-stranded DNA relies on the increased fluorescence that ethidium bromide (EtBr) and other DNA binding labels exhibit when bound to double-stranded DNA. The amplification is carried out in the presence of the label. The increase of double-stranded DNA resulting from the synthesis of target sequences results in a detectable increase in fluorescence, which is monitored during the amplification. Thus, the methods enable monitoring the progress of an amplification reaction.

In a kinetic PCR, the measured fluorescence depends on the total amount of double-stranded DNA present, whether resulting from non-specific amplification or from amplification of the target sequence. Monitoring the fluorescence allows measurement of the increase in the total amount of double-stranded DNA, but the increase resulting from amplification of the target sequence is not measured independently from the increase resulting from non-specific amplification product. The modified primers of the present invention are particularly useful in kinetic PCR because they not only reduce the amount of primer dimer formed, but also delay the formation of detectable amounts of primer dimer. A delay of primer dimer formation until after a significant increase in target sequence has occured enables independent monitoring of the amplification of target sequencs and minimizes the interference from primer dimer.

Kits

The present invention also relates to kits, multicontainer units comprising useful components for practicing the present method. A useful kit contains primers, at least one of which is modified as described herein, for nucleic acid amplification. Other optional components of the kit include, for example, an agent to catalyze the synthesis of primer extension products, the substrate nucleoside triphosphates, appropriate reaction buffers, and instructions for carrying out the present method.

The examples of the present invention presented below are provided only for illustrative purposes and not to limit the scope of the invention. Numerous embodiments of the invention within the scope of the claims that follow the examples will be apparent to those of ordinary skill in the art from reading the foregoing text and following examples.

EXAMPLE 1

Synthesis of Primers Modified with a Benzyl Group

Primers modified by the addition of the benzyl group were synthesized by one of two processes, described below. Primers modifed at the 3' terminal base were synthesized using $N^6$-benzyldeoxyadenosine Controlled Pore Glass (CPG) to initiate the DNA synthesis. Primers modified at an internal base were synthesized using an $N^6$-benzyldeoxyadenosine phosphoramidite.

The following standard abbreviations are used in the example:

| | |
|---|---|
| DMAP | 4-Dimethylaminopyridine |
| DMF | N,N-Dimethylformamide |
| TEA | Triethylamine |
| EDC | 1-Ethyl-3-(3-dimethylaminopropyl) carbodiimide, hydrochloride |
| THF | Tetrahydrofuran |
| DMT | 4,4'-Dimethoxytrityl |
| LCAA-CPG | Long Chain Alkyl Amino controlled pore glass |

I. Synthesis of $N^6$-benzyldeoxyadenosine CPG

Step 1: Synthesis of $N^6$-benzoyl, $N^6$-benzyl, 5'-O-DMT-2'-deoxyadenosine

To $N^6$-Benzoyl-5'-O-(4,4'-dimethoxytrityl)-2'-deoxyadenosine ( 657 mg, 1.0 mmol; Aldrich Chemical Co., Milwaukee, Wisc.), pyridine (10 ml) was added and the mixture was dried by evaporation under vacuum. This was repeated. The resulting foam was dissolved in anhydrous DMF (15 ml; Aldrich Chemical Co., Milwaukee, Wisc.) and cooled to 5° C. Sodium hydride (44 mg, 1.1 mmol, 1.1 equiv. 60% dispersion in oil) was added under an argon atmosphere and stirred at room temperature for 45 minutes. Benzyl bromide (143 µl, 206 mg, 1.2 mmol, 1.2 equiv; Aldrich Chemical Co., Milwaukee, Wisc.) was added over 2 minutes and the mixture was stirred overnight at room temperature. The mixture was dried by evaporation under vacuum and the residue was partitioned between ethyl acetate and water (10 ml each) and extracted. The aqueous phase was re-extracted with ethyl acetate (10 ml) and the combined extracts were dried over anhydrous magnesium sulfate, filtered and evaporated. The crude product was purified by column chromatography on silica gel (75 g) using methanol, triethylamine, methylene chloride (3:0.5:96.5). Fractions containing the product were combined and dried by evaporation to give the expected $N^6$-benzoyl, $N^6$-benzyl, 5'-O-DMT-2'-deoxyadenosine (410 mg, 54%). The structure of the product was confirmed by NMR.

Step 2: Succinylation

To the $N^6$-benzoyl, $N^6$-benzyl, 5'-O-DMT-2'-deoxyadenosine (295 mg, 0.39 mmol), pyridine (10 ml) was added and the mixture was dried by evaporation under high vacuum. This step was repeated. Fresh anhydrous pyridine (10 ml) was added together with succinic anhydride (200 mg, 2 mmol, 5.0 equiv) and DMAP (24 mg), and the solution was stirred under an argon atmosphere overnight at room temperature. The bulk of the solvent was removed under vacuum and the residue was partitioned between methylene chloride (20 ml) and sodium citrate solution (20 ml, 0.1 M, pH 5.0) and extracted. The aqueous phase was extracted with more methylene chloride (20 ml) and the combined extracts were dried over anhydrous sodium sulfate, filtered, and dried by evaporation. The product was purifed by column chromatography on silica gel (4.5 g) using ethyl acetate, triethylamine, methylene chloride (32:1:67) to give the expected 3'-succinate ester, $N^6$-benzoyl-$N^6$-benzyl-3'-O-succinate-5'-O-DMT-2'-deoxyadenosine (247 mg, 74%).

Step 3: Derivatization of CPG

Acid washed CPG was prepared a follows. LCAA-CPG (1.0 g, LCA00500C, 500 angstrom, 88.6 µmol/g; CPG Inc., Fairfield, N.J.) was washed with dichloroacetic acid in dichloromethane (2%, 20 ml) by swirling periodically over 20 minutes at room temperature. The acid washed CPG was filtered on a glass frit and washed with dichloromethane until acid free. The powder was air dried, then dried under vacuum at room temperature overnight.

Coupling of the modified nucleoside intermediate to the acid washed CPG was carried out as follows. To a solution of $N^6$-Benzoyl-$N^6$-benzyl-3'-O-succinate-5'-O-DMT-2'-deoxyadenosine (170 mg, 0.2 mmol), prepared as described above, in dichloromethane (10 ml) was added TEA (100 µL), and the solution was concentrated to approximately 5 ml under an argon atmosphere. DMAP (12 mg, 0.1 mmol, 0.5 equiv), TEA (100 µL), EDC (384 mg, 2.0 mmol, 10 equiv), and the acid-washed CPG from above were added in sequence. Anhydrous pyridine (5 ml) was added and the mixture was sealed and shaken for 3 days at room temperature. The CPG was filtered off under vacuum and washed extensively with isopropanol, then with dichloromethane, air dried, then dried under vacuum for 1 hour.

Capping of the derivatized CPG was carried out as follows. To the dry derivatized CPG were added Cap A and Cap B solutions (5 ml each, Acetic anhydride/2,6-Lutidine/ THF and 10% N-Methylimidazole in THF; Glen Research DNA synthesis reagents, Sterling, Va.) and the mixture was shaken for 4 hours at room temperature. The CPG was filtered off under vacuum and washed extensively with isopropanol, then dichloromethane, air dried, then dried under vacuum overnight.

II. Synthesis of $N^6$-Benzyl Deoxyadenosine Phosphoramidite.

$N^6$-benzoyl, $N^6$-benzyl, 5'-O-DMT-2'-deoxyadenosine was synthesized as described above.

To N 6-benzoyl, N6-benzyl, 5'-DMT-2'-deoxyadenosine (196 mg, 0.26 mmol) in dry THF (8 ml) was added diisopropylethylamine (350 µL, 270 mg, 2.04 mmol, 7.8 equiv) and 2-cyanoethyl N,N-diisopropylchlorophosphoramidite (161 mg, 0.68 mmol, 2.6 equiv.; Aldrich Chemical Co., Milwaukee, Wisc.), and the mixture was stirred for 30 minutes at room temperature under an argon atmosphere. The solvent was removed under vacuum and the residue was partitioned between sodium bicarbonate solution (5%, 20 ml) and ethyl acetate (20 ml). The organic phase was washed with the bicarbonate solution, water, and saturated brine (20 ml each) in sequence, dried over sodium sulfate, filtered, and evaporated. The residue was purified by column chromatography on silica gel (4 g) using acetone/hexane/TEA (34:65:0.7) to yield the desired phosphoramidite (248 mg, 100%).

III. DNA Synthesis purification and analysis.

The benzyl derivatized adenosine CPG (25 mg, 1.0 µmol) was transferred into empty synthesis columns (Glen Research, Sterling, Va.) and these were used to make oligonucleotides on an ABI 374 DNA synthesizer (Perkin Elmer, Applied Biosystems Division, Foster City, Calif.) using conventional synthesis and deprotection conditions. The crude DMT-DNA was purified and converted to the 5'-hydroxy-DNA by standard DMT On/Off HPLC using a Rainin Pure-DNA column on a Rainin HPLC system (Rainin Instrument Co, Woburn, Mass.). The oligonucleotides were analyzed using a ABI capillary electrophoresis system (Perkin Elmer, Applied Biosystems Division, Foster City, Calif.) or by denaturing anion-exchange HPLC chromatography on a Dionex Nucleopak column (Dionex Corp, Sunnyvale, Calif.).

Similarly, synthesis of internally-modified primers was carried out using an unmodified CPG and the modified phosphoramidite synthesized as above.

EXAMPLE 2

Synthesis of Primers Modified with a t-Butyl-benzyl Group

The present example describes the synthesis of primers modified at the 3' terminal adenosine with a p-tert-butylbenzyl group. The modified primers were synthesized essentially as described in Example 1, but using a $N^6$-(p-tert-Butylbenzyl)deoxyadenosine CPG. The synthesis of the derivatized CPG is described below.

Step 1: Synthesis of $N^6$-benzoyl-$N^6$-(p-tert-butylbenzyl)-5'-O-(4,4'-dimethoxytrityl)-2'-deoxyadenosine To $N^6$-benzoyl-5'-O-(4,4'-dimethoxytrityl)-2'-deoxyadenosine (658 mg, 1.0 mmole) was added DMF (anhydrous, 10 ml) and evaporated to dryness. This was repeated. Fresh DMF (10 ml) was added under an Argon atmosphere. Sodium hydride (44 mg, 60% in oil, 1.1 mmole) was added and the mixture was stirred for 0.5 hour at room temperature. 4-(tert-butyl)benzyl bromide (272 mg, 1.2 mmole) was added dropwise and stirred at room temperature overnight. The solvent was removed under vacuum, and the residue was partitioned between ethyl acetate and water (20 ml each). The organic phase was washed with water (3 times, 20 ml), dried over anhydrous magnesium sulfate, filtered and evaporated to dryness. The crude product was purified by column chromatography on silica gel (100 g), using methylene chloride:methanol:triethylamine 96.5:3:0.5 to yield N -benzoyl-N -(p-tert-butylbenzyl)-5'-O-(4,4'-dimethoxytrityl)-2'-deoxyadenosine, (229 mg, 28.5%).

Step 2: Succinylation.

$N^6$-benzoyl-$N^6$-p-tert-butylbenzyl)-5'-O-(4,4'-dimethoxytrityl)-2'-deoxyadenosine (217 mg, 0.27 mmol) w as treated with succinic anhydride (135 mg, 5 equiv)and DMAP (17 mg, 0.5 equiv) in pyridine (10 ml). Work-up and chromatography as described in Example 1, above, yielded $N^6$-benzoyl-$N^6$-(p-tert-butylbenzyl)-5'-O-(4,4'-dimethoxytrityl)-2'-deoxyadenosine, 3'-O-succinate (199 mg, 82%).

Step 3: Derivatization of CPG

The succinate (180 mg, 0.2 mmol) from step 2, above, was treated with the acid washed LCAA-CPG as described in Example 1. The CPG was capped and vacuum dried to yield the $N^6$-benzoyl-$N^6$-(p-tert-butylbenzyl)-5'-O-(4,4'-dimethoxytrityl)-2'-deoxyadenosine, 3'-O-succinate derivatized CPG, (1.065 g).

EXAMPLE 3

Synthesis of Primers Modified with a Methyl Group

Primers modified at the 3' terminal adenosine with a methyl group were synthesized using a $N^6$-methyl dA CPG (22 mg, 1 μmole, Glen Research, Sterling Va.). The $N^6$-methyl dA CPG was placed in an empty synthesis column, and primers were made according to standard conditions of synthesis and deprotection. The primers were purified using the DMT On/Off HPLC procedure as described in Example 1.

EXAMPLE 4

Synthesis of Photo-Labile Modified Primers

The present example describes the synthesis of primers modified at the 3' terminal adenosine with either one or two nitrobenzyl groups. The modified primers were synthesized essentially as described in Example 1, but using either a mononitrobenzyl dA CPG or a bis-nitrobenzyl dA CPG.

I. Mononitrobenzalated primers

The general method for the synthesis of $N^6$-benzoyl-$N^6$-benzyl-2'-deoxyadenosine derivatized CPG (see Example 1) was applied to the synthesis of $N^6$-benzoyl-$N^6$-ortho-nitrobenzyl-2'-deoxyadenosine derivatized CPG, by the substitution of ortho-nitrobenzylbromide as the alkylating agent. Subsequent steps for the CPG were identical to those described in Example 1, with the addition that the intermediates were protected from ambient light by wrapping the reaction flasks in aluminum foil.

Following synthesis of the derivatized CPG, the primers were synthesized as described in Example 1, but were isolated by solid phase extraction using Nensorb Prep disposable columns (NEN Research Products Biotechnology Systems, Du Pont Co, Boston Mass.), using protocols as descibed by the manufacturer.

II. Bis-nitrobenzylated primers

Bis-nitrobenzyl deoxyadenosine CPG was synthesized as described below. Following synthesis of the derivatized CPG, the primers were synthesized and purified as described for the mononitrobenzyl primers.

Step 1: Synthesis of 5'-O-DMT- $N^6$-bis-ortho-nitrobenzyl-2'-deoxyadenosine.

2'-Deoxyadenosine monohydrate (538 mg, 2.0 mmol, Aldrich Chemical, Milwaukee, Wisc.) was dried by evaporation with anhydrous pyridine (2 times, 10 ml) under vacuum. The residue was dissolved in anhydrous DMF (10 ml, Aldrich, Milwaukee, Wisc.) under an argon atmosphere, and sodium hydride (88 mg, 2.2 mmol, 1.1 equiv, 60% dispersion in oil) was added and stirred for 40 mins at room temperature. 2-Nitrobenzyl bromide (710 mg, 3.3 mmol, 1.5 equiv) was added and the solution was stirred for 4 hours at room temperature. The DMF was removed by evaporation under vacuum, and the residue was partitioned between ethyl acetate and water (20 ml each). The aqueous phase was extracted with ethyl acetate (20 ml) and the combined extracts were washed with water (20 ml) and dried over magnesium sulfate, filtered and evaporated. The crude product was purified by column chromatography on silica gel (50 g, using 3% MeOH in $CH_2Cl_2$) to yield 2'-deoxy-$N^6$-bis-ortho-nitrobenzyladenosine (320 mg, 30%).

To 2'-deoxy-N -bis-ortho-nitrobenzyladenosine (200 mg, 0.518 mmol) was added anhydrous pyridine (10 ml) and evaporated to dryness. Pyridine (10 ml) was added followed by 4-4'-dimethoxytrityl chloride (900 mg, 2.3 mmol, 4.5 equiv.) and triethylamine (280 mg, 2.76 mmol, 4.0 equiv.) and stirred at room temperature under an argon atmosphere for 5 hours. Water (0.5 ml) was added and stirred for 20 minutes. The mixture was partitioned between ether and water (20 ml each) and the aqueous phase was re-extracted with ether (20 ml). The extracts were combined and washed with water (20 ml) and dried over anhydrous sodium sulfate, filtered and evaporated. The material was purified by chromatography on silica gel (4 g, using 0.7–2.5% methanol in methylene chloride) to yield 5'-O-DMT- $N^6$-bis-ortho-nitrobenzyl-2'-deoxyadenosine, (121 mg, 33%).

Step 2: Succinylation

5'-O-DMT- $N^6$-bis-ortho-nitrobenzyl-2'-deoxyadenosine (121 mg, 0.145 mmol) was dried by evaporation with anhydrous pyridine (2 times, 3 ml). Pyridine (3 ml), succinic anhydride (58 mg, 0.58 mmol, 4 equiv.) and DMAP (11 mg, catalytic) were added, and the solution was stirred at room temperature for 3 days. The solution was evaporated in vacuo, and the residue was partitioned between methylene chloride (10 ml) and sodium citrate buffer (0.1 M, pH 5.0, 10 ml). The organic phase was dried over anhydrous sodium sulfate, filtered and evaporated to dryness. The crude product was purified by chromatography on silica gel (2 g, using EtOAc: $CH_2Cl_2$:TEA, 32:67:1 10 ml, then MeOH:$CH_2Cl_2$, 3:97, 25 ml) to yield a pale yellow foam, 5'-O-DMT-$N^6$-bis-ortho-nitrobenzyl-2'-deoxyadenosine-3'-O-succinate, (138 mg, 99.5%).

Step 3: Derivatization of the CPG

Acid-washed LCAA-CPG was prepared as in Example 1.

Coupling of the modified nucleoside intermediate to the acid wached CPG was carried out as follows. 5'-O-DMT- N -bis-ortho-nitrobenzyl-2'-deoxyadenosine-3'-O-succinate (37 mg, 0.04 mmol) was treated with TEA (16 μl) in an amber colored glass vial, and evaporated. To this residue was added anhydrous pyridine (1.5 ml), TEA (2 μl), DMAP (2.4 mg), EDC (76 mg, 0.04 mmol) and acid-washed LCAA-CPG (200 mg), and the mixture was shaken on an orbital mixer for three days at room temperature. The CPG was filtered off under reduced pressure and washed extensively with isopropanol, then with methlene chloride, air dried, then dried under vacuum for 1 hour.

Capping of the derivatized CPG was carried out as described in Example 1.

EXAMPLE 5

Amplifications using Modified Primers—Effect of Position of Modified Nucleotide To demonstrate the effect of the modified primers on the formation of primer dimer, comparisons were carried out of amplifications of HIV-1 RNA using both modified primers and unmodified primers. In addition, to assess the effect of the position of the modified nucleotide on the reduction of primer dimer, amplifications were carried out using three different upstream modified primers, which differed only in the location of the modified base.

Target Nucleic Acid

HIV-1 RNA templates were synthesized using an HIV-1 RNA transcription vector essentially as described in Mulder et al., 1994, J. Clin. Microbiol. 32(2):292–300.

Primers

Amplifications were carried out using both unmodified and modified primers. The nucleotide sequences of the unmodified primers are shown below, oriented in the 5' to 3' direction. Upstream primer RAR1032MB (SEQ ID NO: 1) and downstream primer RAR1033MB (SEQ ID NO: 2) amplify a 175 base pair product corresponding to nucleotide positions 2956 to 3130 of the sequence of HIV-1 reference strain HXB2 (GenBank accession no. K03455).

| Primer | Seq. ID No. | Sequence |
| --- | --- | --- |
| RAR1032MB | 1 | CAATGAGACACCAGGAATTAGATATCAGTACAA |
| RAR1033MB | 2 | CCCTAAATCAGATCCTACATATAAGTCATCCA |

The above primer designations refer to the unmodified primers. Unmodified primers were biotinylated at the 5' end. Modified primers were synthesized as described in Example 1, which consisted of the same nucleotide sequences as the unmodified primers, but containing a benzylated adenosine at either the 3' terminal position or at a position one or three nucleotides upstream of the 3' terminus. The modified forms of the primers are designated herein as follows:

Modified HIV-1 Amplification Primers

| Primer | Seq Id. No. | Position of Modified Nucleotide |
| --- | --- | --- |
| RAR1032MBA1 | 1 | 3' terminus |
| RAR1032MBA2 | 1 | 1 from 3' terminus |
| RAR1032MBA4 | 1 | 3 from 3' terminus |
| RAR1033MBA1 | 2 | 3' terminus |

Amplification

Amplifications were carried out in 100 µl reactions containing the following reagents:

100 copies of HIV template RNA
50 mM Tricine (pH 8.33),
110 mM KOAc,
300 µM each dATP, dCTP, and dGTP,
50 µM dTTP
500 µM dUTP,
50 µM of each primer,
3.5 mM Mn(OAc)$_2$,
13% Glycerol.
20 units of Z05 DNA polymerase*, and
2.0 units of UNG**.

\* described in U.S. Pat. No. 5,455,170
\*\* manufactured and developed by Hoffmann-La Roche and marketed by Perkin Elmer, Norwalk, Conn.

Amplification temperature cycling was carried out in a TC480 DNA thermal cycler (Perkin Elmer, Norwalk, Conn.) using the following temperature profile:

| | |
| --- | --- |
| Pre-reaction incubation | 45° C. for 4 minutes; |
| Reverse-transcription | 60° C. for 20 minutes; |
| 46 cycles: | denature at 94° C. for 45 seconds, anneal/extend at 60° C. for 45 seconds; |
| Final extension | 60° C. for 7 minutes; |
| Post-reaction hold | 10° C. until analysis (for a short time). |

Detection of Amplified Product

The presence of amplified product was detected by gel electrophoresis as follows. Reaction products were fractionated using an agarose gel (100 ml of 3% NuSieve and 0.5% SeaChem) and 1×TBE (0.089 M Tris, 0.089 M boric acid, 0.0025 M disodium EDTA) running buffer were used. Ethidium bromide (0.5 µg/ml) was added to stain any DNA present. Electrophoresis was carried out at 100 volts for approximately 1 hour. The ethidium bromide-stained bands of DNA were visualized using UV irradiation.

Results

The results of the gel electrophoretic analysis are seen in FIG. 1. The lane numbers corresponding to each of the amplifications using combinations of the unmodified and modified primers are shown in the table below. The bands corresponding to the intended HIV product are indicated in the figure by an arrow. The other bands in the gel correspond to non-specific amplification product and, in particular, primer dimer.

| Primers | | |
| --- | --- | --- |
| Upstream | Downstream | Lane No. |
| RAR1032MB | RAR1033MB | 1 |
| RAR1032MBA1 | RAR1033MB | 2 |
| RAR1032MBA2 | RAR1033MB | 3 |
| RAR1032MBA4 | RAR1033MB | 4 |
| RAR1032MB | RAR1033MBA1 | 5 |
| RAR1032MBA1 | RAR1033MBA1 | 6 |
| RAR1032MBA2 | RAR1033MBA1 | 7 |
| RAR1032MBA4 | RAR1033MBA1 | 8 |

Because the formation of primer dimer competes with the formation of the intended amplification product, a reduction in primer-dimer typically results in a concomitant increase in the amount of intended product formed. Thus, the effect of the modified primers can be seen by comparing the amount of primer-dimer formed relative to the amount formed using unmodified primers and by comparing the amount of intended target formed relative to the amount formed using unmodified primers.

A comparison of the results using two unmodified primers (lane 1) to the results using a single 3'-modified primer (lanes 2 and 5) and to the results using two 3'-modified primers (lane 6) indicates that a decrease in primer dimer was obtained using either one or two modified primers. In amplifications using a single 3'-modified primer, a small difference in the reduction of primer dimer was seen which depended on which primer was modified. The use of two modified primers (lane 6) resulted in both the greatest decrease in primer dimer and a detectable increase in the amount of amplified target sequence.

The effect of the position of the modified nucleotide is seen in a comparison of lanes 6–8. The reduction of primer dimer obtained using a primer modified at the nucleotide adjacent to the 3' terminal nucleotide (lane 7) was equivalent to that obtained using a primer modified at the 3' terminal nucleotide (lane 6), whereas the improvement obtained using a primer modified at the nucleotide three bases upstream of the 3' terminal nucleotide (lane 8) was slightly less.

EXAMPLE 6

Further Amplifications using Modified Primers—Effect of Position of Modified Nucleotide To further demonstrate the effect of the modified primers on the formation of primer dimer, comparisons were carried out of amplifications of HCV RNA using both modified primers and unmodified primers, essentially as described above. Amplifications were carried out using three different modified downstream primers, which differed only in the location of the modified base.

Target Nucleic Acid

HCV RNA templates were synthesized using an HCV RNA transcription vector as described in Young et al., 1993, J. Clin. Microbiol. 31(4):882–886.

Primers

Amplifications were carried out using both unmodified and modified primers. The nucleotide sequences of the unmodified primers are shown below, oriented in the 5' to 3' direction. Upstream primer ST280A (SEQ ID NO: 3) and downstream primer ST778AA (SEQ ID NO: 4) amplify a 240 base pair product from the 5' untranslated region of the HCV genome.

HCV Amplification Primers

| Primer | Seq Id No: | Nucleotide Sequence |
|---|---|---|
| ST280A | 3 | GCAGAAAGCGTCTAGCCATGGCGTTA |
| ST778AA | 4 | GCAAGCACCCTATCAGGCAGTACCACAA |

The above primer designations refer to the unmodified primers. Modified primers were synthesized as described in Example 1, which consisted of the same nucleotide sequences as the unmodified primers, but contained a benzylated adenosine at either the 3' terminal position or at a position one or three nucleotides upstream of the 3' terminus. The modified forms of the primers are designated herein as follows:

Modified HCV Amplification Primers

| Primer | Seq Id. No. | Position of Modified Nucleotide |
|---|---|---|
| ST280ABA1 | 3 | 3' terminus |
| ST778AABA1 | 4 | 3' terminus |
| ST778AABA2 | 4 | 1 from 3' terminus |
| ST778AABA4 | 4 | 3 from 3' terminus |

Amplification and Analysis

Amplifications were carried out essentially as described in Example 3, but using 100 copies of HCV RNA template. Gel analysis of the amplified product was carried out as described in Example 3.

Results

Figure 2:
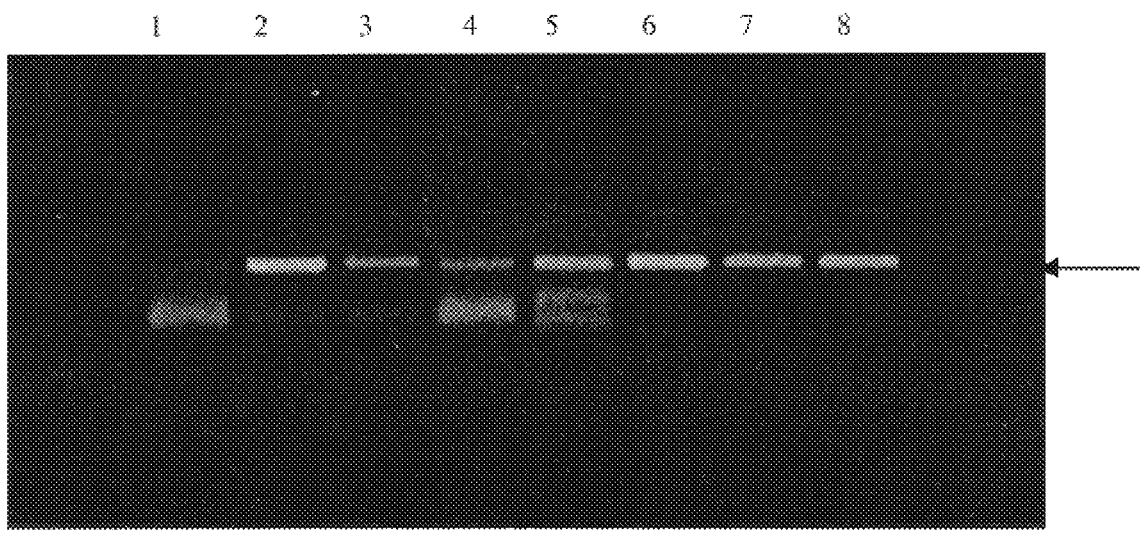
FIG. 2 shows the results of amplifications of HCV RNA carried out using benzylated primers, as described in Example 6.

The results of the gel electrophoretic analysis are seen in FIG. 2. The lane numbers corresponding to each of the amplifications using combinations of the unmodified and modified primers are shown in the table below. The bands corresponding to the intended HCV product are indicated in the figure by an arrow. The other bands in the gel correspond to non-specific amplification product and, in particular, primer dimer.

| Primers | | |
|---|---|---|
| Upstream | Downstream | Lane No. |
| ST280A | ST778AA | 1 |
| ST280A | ST778AABA1 | 2 |
| ST280A | ST778AABA2 | 3 |
| ST280ABA | ST778AABA4 | 4 |
| ST280ABA1 | ST778AA | 5 |
| ST280ABA1 | ST778AABA1 | 6 |
| ST280ABA1 | ST778AABA2 | 7 |
| ST280ABA1 | ST778AABA4 | 8 |

Because the formation of primer dimer competes with the formation of the intended amplification product, a reduction in primer-dimer typically results in a concomitant increase in the amount of intended product formed. Thus, the effect of the modified primers can be seen both by comparing the amount of primer-dimer formed relative to the amount formed using unmodified primers and by comparing the amount of intended target formed relative to the amount formed using unmodified primers.

The results obtained were similar to those obtained from the HIV amplifications described in the previous example, but in the HCV amplifications, the increase in intended product was more apparent than in the HIV amplifications. A comparison of the results using two unmodified primers (lane 1) to the results using a single 3'-modified primer (lanes 2 and 5) and to the results using two 3'-modified primers (lane 6) indicates that a decrease in primer dimer was obtained using either one or two modified primers. The use of two modified primers (lane 6) resulted in both the greatest decrease in primer dimer along with a significant increase in the amount of amplified target sequence. As in the previous example, a small difference in the reduction of primer dimer was seen in amplifications using a single 3'-modified primer that depended on which primer was modified.

The effect of the position of the modified nucleotide is seen in a comparison of lanes 6–8. Essentially equivalent results were obtained using primers modified at the 3'-terminal nucleotide (lane 6), nucleotide adjacent to the 3'-terminal nucleotide (lane 7), and the nucleotide three bases upstream of the 3'-terminal nucleotide (lane 8). These results indicate that the modifier group can be attached to any of the four nucleotides at the 3' end of the primer.

EXAMPLE 7

Amplifications using Modified Primers—Effect of Modifier Group

To further demonstrate the effect of the modified primers on the formation of primer dimer, and to demonstrate alternative primer modifications, comparisons were carried out of amplifications of HCV RNA using both modified primers and unmodified primers, wherein the primers were modified by the addition of one of three different modifier groups: benzyl, nitrobenzyl, and methyl groups.

Amplification results were analyzed by two different methods. In one set of comparisons, the presence of primer-dimer was assayed by gel electrophoretic analysis of the reaction products. In a second set of comparisons, the formation of primer dimer was monitored during amplification using the kinetic PCR methods described above.

Target Nucleic Acid

HCV RNA templates were synthesized using an HCV RNA transcription vector as described in Young et al., 1993, J. Clin. Microbiol. 31(4):882–886.

Amplification Primers

Amplifications were carried out using both unmodified and modified primers. The modified primers consisted of the same nucleotide sequences as the unmodified primers, but were modified at the 3' terminal adenosine by the addition of a methyl group, an benzyl group, or a nitrobenzyl group. Primers were synthesized as described in the previous examples. The designations for the primers used are shown below.

| Primer | Seq Id. No. | Modification of 3' Base |
|---|---|---|
| ST280A | 3 | unmodified |
| ST280AMEA1 | 3 | methyl |
| ST280ABA1 | 3 | benzyl |
| ST280ANBA1 | 3 | nitrobenzyl |
| ST778AA | 4 | unmodified |
| ST778AAMEA | 4 | methyl |
| ST778AABA1 | 4 | benzyl |
| ST778AANBA1 | 4 | nitrobenzyl |

Amplification Reactions

Amplifications were carried out in 100 $\mu$l reactions containing the following reagents:

0, 20, or 200 copies HCV RNA template 50 mM Tricine, pH 8.3;

110mM KOAc;

3.5 mM $Mn(OAc)_2$;

300 $\mu$M each dATP, dCTP, dGTP;

50 $\mu$M dTTP;

500 $\mu$M dUTP;

250 nM each primer;

20 U rTth*;

2U UNG*; and

13% Glycerol.

* manufactured and developed by Hoffmann-La Roche and marketed by Perkin Elmer, Norwalk, Conn.

Thermal cycling of each reaction mixture was carried out in a GeneAmp® PCR System 9600 thermal cycler (Perkin Elmer, Norwalk, Conn.) using the following temperature profile:

| Pre-reaction incubation | 45° C. for 4 minutes; |
|---|---|
| Reverse-transcription | 60° C. for 24 minutes; |
| 46 cycles: | denature at 94° C. for 30 seconds, anneal/extend at 60° C. for 30 seconds; |
| Final extension | 60° C. for 7 minutes |
| Post-reaction hold | 4° C. |

Detection of Amplified Product

A. Gel Electrophoresis

The presence of amplified product was detected by gel electrophoresis as follows. Reaction products were fractionated using an agarose gel (100 ml of 3% NuSieve, 0.5% SeaChem, and 0.5 $\mu$g/ml ethidium bromide) and 1×TBE (0.089 M Tris, 0.089 M boric acid, 0.0025 M disodium EDTA) running buffer. Electrophoresis was carried out at 100 volts for approximately 1 hour. The ethidium bromide-stained bands of DNA were visualized using UV irradiation.

B. Detection by Kinetic PCR

In the kinetic PCR methods described above, a intercalating dye such as ethidium bromide, which fluoresces more strongly when intercalated into double-stranded DNA, is added to the PCR. The increase in double-stranded DNA during amplification is monitored by measuring the fluorescence of the dye during the reaction. Because the kinetic PCR methods only measure an increase in the total amount of double-stranded DNA, formation of non-specific amplification product is not measured independently. In order to measure the occurence of non-specific amplification resulting from primer-dimer independent of template amplification, reactions were carried out without template nucleic acid. In such template-free reactions, any increase in double-stranded DNA is attributable to the formation of template-independent, non-specific amplification product.

Kinetic PCR reaction conditions were as described above, except that ethidium bromide was added to the reaction mixture at a concentration of 1 Mg/ml. Reactions were monitored by measuring the fluorescence of the reaction mixture as described in copending U.S. patent application Ser. No. 08/266,061, incorporated herein by reference.

Fluorescence measurements were normalized by dividing by an initial fluorescence measurement obtained during a cycle early in the reaction while the fluorescence measurements between cylces were relatively constant. The cycle number chosen for the initial fluorescence measurment was the same for all reactions compared, so that all measurements represent increases relative to the same reaction cycle. Reaction fluorescence in target-free reactions remained relatively constant until primer dimer formed. In most reactions, if enough amplification cycles are carried out, primer dimer eventually becomes detectable. The effect of the modified primers can be seen from a comparison of the number of cycles carried out until primer dimer is formed, if at all.

Results

Figure 3:
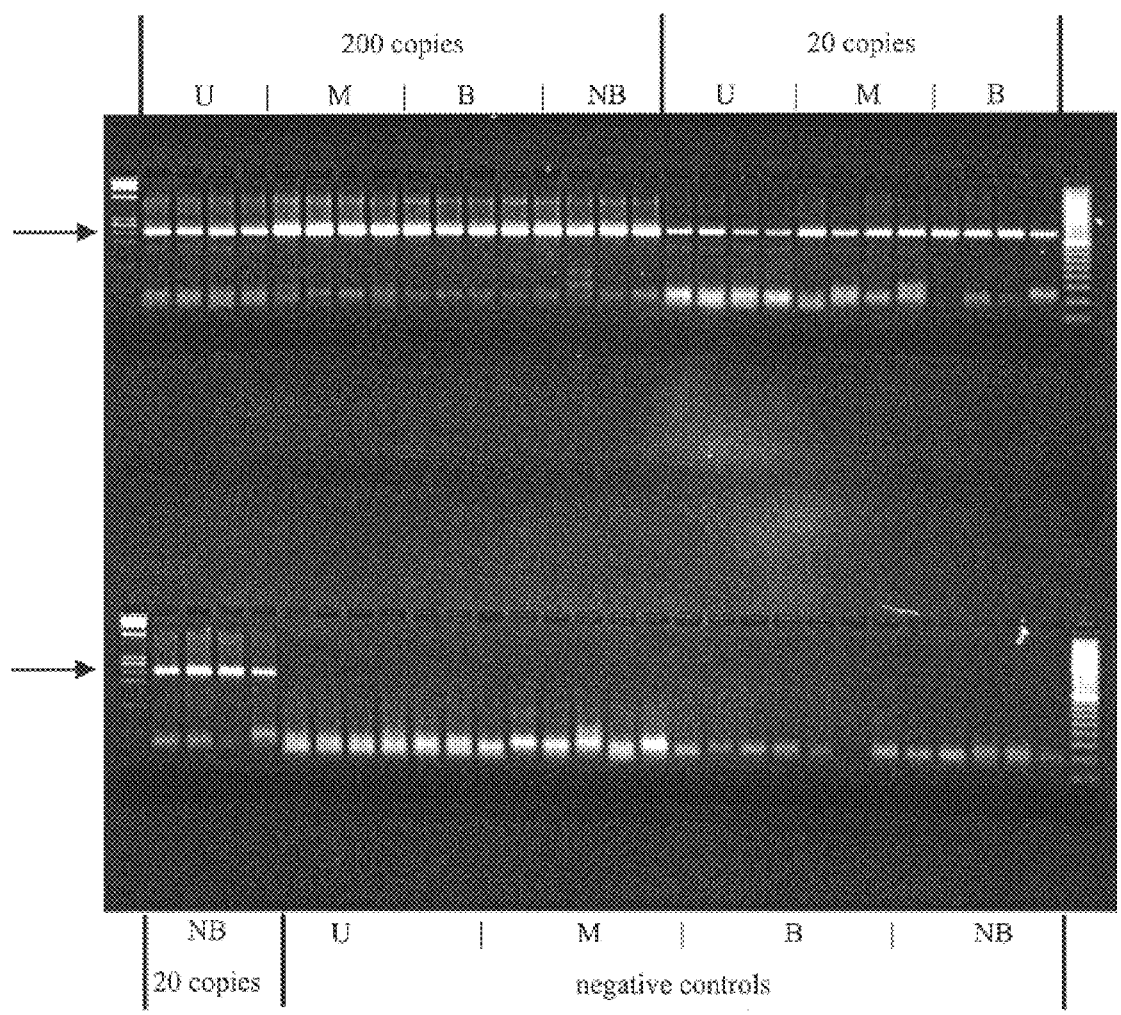
FIG. 3 shows the results of amplifications of HCV RNA carried out using primers modified with one of three modifier groups, as described in Example 7.

The results of the gel electrophoretic analysis are seen in FIG. 3. The lane numbers corresponding to each of the amplifications using the unmodified and three types of modified primers and 200 copies, 20 copies, or 0 copies of HCV RNA are shown in the table below (lanes numbers are counted from left to right: lanes 1–30 are in the top half of the gel; lanes 31–60 are in the bottom half of the gel). In addition, molecular weight markers were present in lanes 1 and 31 (Hae III digested PhiX 174 RF DNA, New England Bioloabs, Beverly, Mass.) and in lanes lanes 30 and 60 (Superladder-low, 20 bp ladder, Gen Sura, Del Mar, Calif.). The bands corresponding to the intended specific product are indicated in the figure by an arrow (~230 bp). The other bands in the gel correspond to non-specific amplification product and, in particular, primer dimer.

Lane Numbers of Amplifications Results Shown in FIG. 3

| Templates | Primers | Lanes |
|---|---|---|
| 200 | unmodified | 2–5 |
| 200 | methylated | 6–9 |
| 200 | benzylated | 10–13 |
| 200 | nitrobenzylated | 14–17 |

-continued

| Templates | Primers | Lanes |
|---|---|---|
| 20 | unmodified | 18–21 |
| 20 | methylated | 22–25 |
| 20 | benzylated | 26–29 |
| 20 | nitrobenzylated | 32–35 |
| 0 | unmodified | 36–41 |
| 0 | methylated | 42–47 |
| 0 | benzylated | 48–53 |
| 0 | nitrobenzylated | 54–59 |

The results demonstrate that amplification using the modified primers resulted in a greater amount of amplified HCV nucleic acid than amplifications using the unmodified primers. In addition, amplification using the modified primers resulted in a reduction in primer dimer relative to amplifications using the unmodified primers.

In the kinetic PCR assays, the fluorescence was monitored throughout the reaction. The rate of increase of fluorescence after the increase in fluorescence was detectable was approximately the same in all reactions, as evidenced by the shape of the curve obtained plotting fluorescence versus cycle number (not shown). This indicated that the modified primers do not detectably inhibit the efficiency of each amplification step after the initial stage of amplification. The reactions differed significantly in the number of cycles carried out before an increase in fluorescence was detectable.

To quantify the differences among the reactions, the results are expressed in terms of the number of amplification cycles carried out until the fluorescence exceeded an arbitrary fluorescence level (AFL). The AFL was chosen close to the baseline fluorescence level, but above the range of random fluctuations in the measured fluorescence, so that the reaction kinetics were measured during the geometric growth phase of the amplification. Accumulation of amplified product in later cycles inhibits the reaction and eventually leads to a reaction plateau.

The kinetic PCR results are summarised in the table below. Each value for amplifications of 20 or 200 copies of target template represents an average of five replicate amplifications, with the exception of amplifications using benzylated primers and 20 copies of target, which represent an average of four replicates. Each value for amplifications without template represents an average of eight replicates.

Two out of the eight replicates of amplifications using benzylated primers with no target present did not result in primer dimer formation by the end of the 46 cycles. The average of the remaining six amplifications is shown, which represents an average conditioned on primer dimer being formed. The conditional average is not comparable to the other values shown because of the deleted data.

Cycles to Reach AFL

| | Target copy number | | |
|---|---|---|---|
| Primer | 0 | 20 | 200 |
| unmodified | 35 | 36 | 34 |
| methyl | 39 | 38 | 36 |
| nitrobenzyl | 43 | 40 | 37 |
| benzyl | (43*) | 41 | 37 |

*2/8 showed no primer dimer formation

The data indicate that the modified primers apparently delay the amplification of target nucleic acid such that the AFL is reached several cycles later. The delay did not correspond to a reduction in the final yield of specific amplification product. All amplifications of target nucleic acid were observed to reach a plateau within the 46 cycles used in the experiment and, as evidenced by the corresponding data from the gel electrophoretic analysis, the final yield was increased using the modified primers.

The data indicate that the delay in the formation of primer dimer was significantly greater than the delay in the amplification of target. The benificial effect of the primers is most clearly seen comparing target-free amplifications and amplifications of 200 copies of template. Using unmodified primers, the increase in fluorescence to the AFL occured only one cycle later in amplifications without target, which indicates that amplification of target would be difficult to distinguish from the formation of primer dimer. In contrast, using modified primers, the increase in fluorescence due to primer dimer occured at least three cycles later and, using the benzylated primers, occured at least 6 cycles later, if it occured at all. Thus, target amplification could be detected and distinguished from the formation of primer dimer.

Comparing target-free amplifications and amplifications of 20 copies of template, the effect of the modified primers showed the same pattern of a greater delay in the onset of primer dimer than the delay in target amplification. Using unmodified primers, 20 copies of template could not be detected. Using the nitrobenzyl and benzyl primers, the formation of primer dimer was delayed sufficiently so as to enable the detection of 20 copies of template in this system.

The data from monitoring the fluorescence at each amplification cycle (data not shown), indicated that, in general, the delay in primer dimer formation was sufficient to prevent primer dimer formation from reaching a plateau level within the 46 cycles. Thus, the modified primers appeared to delay the formation of primer dimer sufficiently such that amplification of target can be completed and the reaction stopped before a significant level of primer dimer is formed.

EXAMPLE 8

Photo-Labile Primers

To demonstrate the use of photo-labile modified primers, amplifications of HCV RNA were carried out using both modified primers and unmodified primers. The modified primers were modified by the attachment of one or two nitrobenzyl groups to the exocyclic amine of the 3' terminal adenine.

Amplification Primers

Primers were synthesized as described in Example 4. The designations for the primers used are shown below.

| Primer | Seq Id. No. | Modification of 3' Base |
|---|---|---|
| ST280A | 3 | unmodified |
| 15239 | 3 | bis-nitrobenzyl |
| 15241 | 3 | mononitrobenzyl |
| ST778AA | 4 | unmodified |
| 15240 | 4 | bis-nitrobenzyl |
| 15242 | 4 | mononitrobenzyl |

Amplification Reactions

For each primer pair, reactions were carried out using a dilution series of input target concentration. Two panels of the reactions, each including all combinations of primer pair and input target concentration, were carried out, and within each reaction panel, each reaction containing a given primer pair and target concentration was carried out in duplicate.

Amplifications were carried out in 100 μl reactions containing the following reagents:

0, 10, 10², 10³, 10⁴ or 10⁵ copies HCV RNA template
55 mM Tricine, 90 mM KOAc,
3 mM Mn(OAc)₂,
200 μM each dATP, dCTP, dGTP, dTTP,
200 μM dUTP,
250 nM each primer,
10 U rTth*,
2 U UNG*, and
8% Glycerol.

* manufactured and developed by Hoffmann-La Roche and marketed by Perkin Elmer, Norwalk, Conn.

Thermal cycling of each reaction mixture was carried out in a GeneAmp PCR System 9600 thermal cycler (Perkin Elmer, Norwalk, Conn.) using the following temperature profile:

| Pre-reaction incubation | 50° C. for 5 minutes; |
|---|---|
| Reverse-transcription | 60° C. for 30 minutes; |
| Initial denaturation | 95° C. for 1 minute; |
| 2 cycles: | denature at 95° C. for 15 seconds, anneal/extend at 60° C. for 20 seconds; |
| 46 cycles: | denature at 90° C. for 15 seconds, anneal/extend at 60° C. for 20 seconds; |
| Final extension | 72° C. for 10 minutes |

Polished reaction tube caps (Perkin Elmer, Norwalk, Conn.) were used throughout. After the reaction temperature was raised to 60° C. for the reverse-transcription step, the heated lid was removed from the PCR tray in the block of the thermal cycler, and half of the reaction tubes (one complete set of the duplicate reactions) were covered with aluminum foil. The other half was illuminated using a hand-held UV lamp emitting at 302 mn (UVP model UVM-57, UVP Products, San Gabriel, Calif.) for ten minutes. The heated cover was replaced and the amplification was continued.

Results

Figure 4:
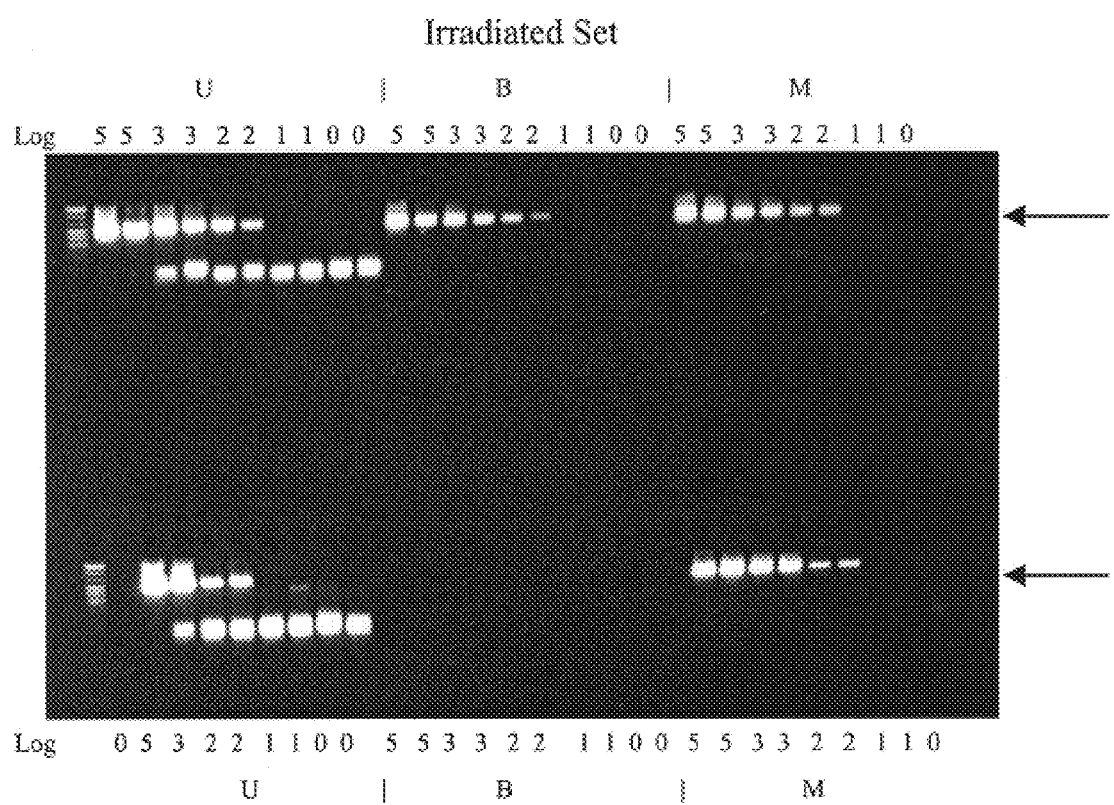
FIG. 4 shows the results of amplifications of HCV RNA carried out using photo-labile modified primers, as described in Example 8.

The results of the amplifications were analyzed by gel electrophoresis as described above. The results are seen in FIG. 4. The primers and template copy number used in each reaction are indicated in the gel (log of the copy number shown). The bands corresponding to the intended product are indicated in the figure. The other bands in the gel correspond to non-specific amplification product and, in particular, primer dimer.

A comparison of the UV-irradiated set of reactions shows that the use of the modified primers resulted in a significant decrease in primer dimer, especially at low copy numbers.

A comparison of the non-irradiated set of reactions shows that the use of the bis-nitrobenzyl primers resulted in a complete inhibition of the amplification, as expected. Amplifications using the mononitrobenzyl primers not only yielded product, but exhibited a significant decrease in primer dimer, which is consistant with the results obtained in the previous example.

EXAMPLE 9

Amplifications using p-tert-butylbenzyl-Modified Primers

This example describes the amplification of HCV RNA using primers modified with p-tert-butylbenzyl groups.

Target Nucleic Acid

HCV RNA templates were synthesized using an HCV RNA transcription vector as described in Young et al., 1993, J. Clin. Microbiol. 31(4):882–886.

Primers

Amplifications were carried out using modified primers synthesized as described in Example 2, above. The nucleotide sequences of the unmodified primers are shown below, oriented in the 5' to 3' direction. The primers used were modified versions of upstream primer ST280A (SEQ ID NO: 3) and downstream primer ST778AA (SEQ ID NO: 4). The modified forms of the primers are designated herein as follows:

Modified HCV Amplification Primers

| Primer | Seq Id. No. | Position of Modified Nucleotide |
|---|---|---|
| ST280ATBU | 3 | 3' terminus |
| ST778AATBU | 4 | 3' terminus |

Amplification and Analysis

Amplifications were carried out in 100 μl reactions containing the following reagents:

20, 5, 2.5, 2, or 0 copies of HCV template RNA
50 mM Tricine (pH 8.33),
110 mM KOAc,
300 μM each dATP, dCTP, and dGTP,
50 μM dTTP
500 μM dUTP,
50 nM of each primer,
3.5 mM Mn(OAc)₂,
13% Glycerol.
20 units of rTth DNA polymerase, and
8.0 units of UNG*.

* manufactured and developed by Hoffmann-La Roche and marketed by Perkin Elmer, Norwalk, Conn.

Amplification temperature cycling was carried out in a TC480 DNA thermal cycler (Perkin Elmer, Norwalk, Conn.) using the following temperature profile:

| Pre-reaction incubation | 45° C. for 12 minutes; |
|---|---|
| UNG inactivation | 90° C. for 30 seconds; |
| Reverse-transcription | 60° C. for 20 minutes; |
| 47 cycles: | denature at 94° C. for 45 seconds, anneal/extend at 60° C. for 70 seconds; |
| Final extension | 60° C. for 7 minutes; |
| Post-reaction hold | 10° C. until analysis (for a short time). |

The amplification products were analyzed by gel electrophoresis, as described above.

Results

Amplifications carried out at each target template number were replicated as follows: 3 amplifications were carried out using 20 copies of target template, 3 amplifications were carried out using 5 copies of target template, 2 amplifications were carried out using 2.5 copies of target template, 1 amplification was carried out using 2 copies of target template, and 23 amplifications were carried out with no target present. All template positive amplifications resulted in a single band on the gel of the expected target size. None of the amplifications resulted in either primer dimer or other non-specific amplification product.

The results can be compared to those in Example 6, above, wherein the same HCV target was amplified using the same primer sequences. A comparison of these results to those in Example 6 indicate that amplifications using p-tert-butylbenzyl-modified primers were significantly improved relative to the corresponding amplifications carried out with unmodified primers.

Additional experiments were carried out in which HIV-1 RNA was amplified using p-tert-butylbenzyl-modified versions of the primers described in Example 5, above. The amplifications were carried out essentially as described above. As with the HCV system described herein, all HIV-1 template positive amplifications resulted in a single band on the gel of the expected target size, and none of the amplifications resulted in either primer dimer or other non-specific amplification product.

These additional results can be compared to those in Example 5, above, wherein the same HIV target was amplified using the same primer sequences. A comparison of these results to those in Example 5, above, indicates that amplifications using p-tert-butylbenzyl-modified primers were significantly improved relative to the corresponding amplifications carried out with unmodified primers.

EXAMPLE 10

Amplification of Mycobacterial DNA

This example describes a comparison of amplifications of mycobacterial DNA carried out using unmodified and modified primers. Both primers modified by the addition of a benzyl group to the 3' terminal nucleotice and primers modified by the addition of a p-tert-butylbenzyl group to the 3' terminal nucleotide were used. The reactions using unmodified primers were essentially as described in Tevere et al., 1996, J. Clin. Microbiol. 34(4):918–923. Amplifications were carried out using sputum samples into which mycobacterial DNA had been added in a known concentration to mimic infected clinical samples. Additional amplifictions were carried out using purified mycobacterial DNA, and using DNA-free negative control samples.

Sample Preparation

Sputum specimens previously shown to be negative for mycobacteria by microscopy and culture were liquefied and decontaminated by the N-acetyl-cysteine-NaOH method recommended by the CDC (Kent and Kubica, 1985, Public Health Mycobacteriology—a guide for the level III laboratory, U.S. Department of Health and Human Services, Centers for Disease Control, Atlanta, incorporated herein by reference). Liquefied sputum (100 μl) was added to 500 μl of Respiratory Specimen Wash Reagent (10 mM Tris-HCl, 1 mM EDTA, 1% (v/v) Triton X-100, 0.05% NaN$_3$, pH8.0) and centrifuged for 10 minutes at 12,500×g. Each pellet was resuspended in 100 μl of lysis reagent (0.05 N NaOH, 1% (v/v) Triton X-100, 1 mM EDTA, 0.05% NaN$_3$) and incubated for 45 minutes at 60° C. The lysates were then neutralized with 100 μl of neutralization reagent (0.2 M Tris-HCl, 8 mM MgCl$_2$, 0.05% NaN$_3$, pH 7.5).

Pooled sputum lysates were generated by combining 80 μl each of two separate sputum lysates. To each of 8 pooled sputum lysates (160 μl each) were added 15 μl of a DNA stock (2 copies/μl in a 1:1 mixture of lysis and neutralization reagents) purified from cultured M tuberculosis.

Samples containing purified mycobacterial DNA (no sputum) in a known concentration were prepared by adding 10 μl of the DNA stock to 100 μl of a 1:1 mixture of lysis reagent and neutralization reagent.

Negative control samples (no DNA) consisted a mixture of 100 μl of lysis reagent and 100 μl of neutralization reagent.

Amplification Primers

Amplifications were carried out using primers consisting of the following nucleotide sequences:

| Primers | | Sequence |
|---|---|---|
| KY18 | (SEQ ID NO:5) | 5'-CACATGCAAGTCGAACGGAAAGG-3' |
| KY436 | (SEQ ID NO:6) | 5'-TAACACATGCAAGTCGAACGGAAA-'3' |
| KY75 | (SEQ ID NO:7) | 5'-GCCCGTATCGCCCGCACGCTCACA-3' |

The following primer pairs, containing the indicated modifier group attached to the 3' terminal base, were used in the amplifications. All modified primers were synthesized as described in the previous examples. All primers were biotinylated at the 5' end.

| Primer Pair | Primer Sequences | Modification |
|---|---|---|
| A | KY18 (SEQ ID NO: 5) | unmodified |
|   | KY75 (SEQ ID NO: 7) | unmodified |
| B | KY436 (SEQ ID NO: 6) | benzyl |
|   | KY75 (SEQ ID NO: 7) | benzyl |
| C | KY436 (SEQ ID NO: 6) | p-tert-butylbenzyl |
|   | KY75 (SEQ ID NO: 7) | p-tert-butylbenzyl |

Amplification

For each sample, amplifications were carried out using the unmodified primer pair, KY18 (SEQ ID NO: 5) and KY75 (SEQ ID NO: 7), and modified forms of the primer pair, KY436 (SEQ ID NO: 6) and KY75 (SEQ ID NO: 7).

Amplifications were carried out in 100 μl reactions, each containing 50 μl of one of the three samples described above and 50 μl of a 2×reagent mixture, which contains the following reagents:

100 mM Tris-HCl, pH 8.9;
500 nM each primer;
200 μM (each) dNTP (dATP, dCTP, dGTP, dUTP);
20% (v/v) glycerol;
10 units AmpliTaq®*;
6 units AmpErase®*

* Manufactured and developed by Hoffmann-La Roche and marketed by Perkin Elmer (Norwalk, Conn.;

Thermal cycling of each reaction was carried out in a GeneAmp PCR system 9600 thermal cycler (Perkin Elmer, Norwalk, Conn.) using the following temperature profile:

| | |
|---|---|
| Pre-reaction incubation | 50° C. for 5 minutes; |
| 2 cycles: | denature at 98° C. for 20 seconds, anneal at 62° C. for 20 seconds, extend at 72° C. for 45 seconds; |
| 41 cycles: | denature at 94° C. for 20 seconds, anneal at 62° C. for 20 seconds, extend at 72° C. for 45 seconds; |
| Final extension | 72° C. for approximately 12 hours (overnight). |

Amplification products were visualized by electrophoresis through a 2% Nusieve®, 0.5% agarose gel followed by ethidium bromide staining.

Results

Figure 5:
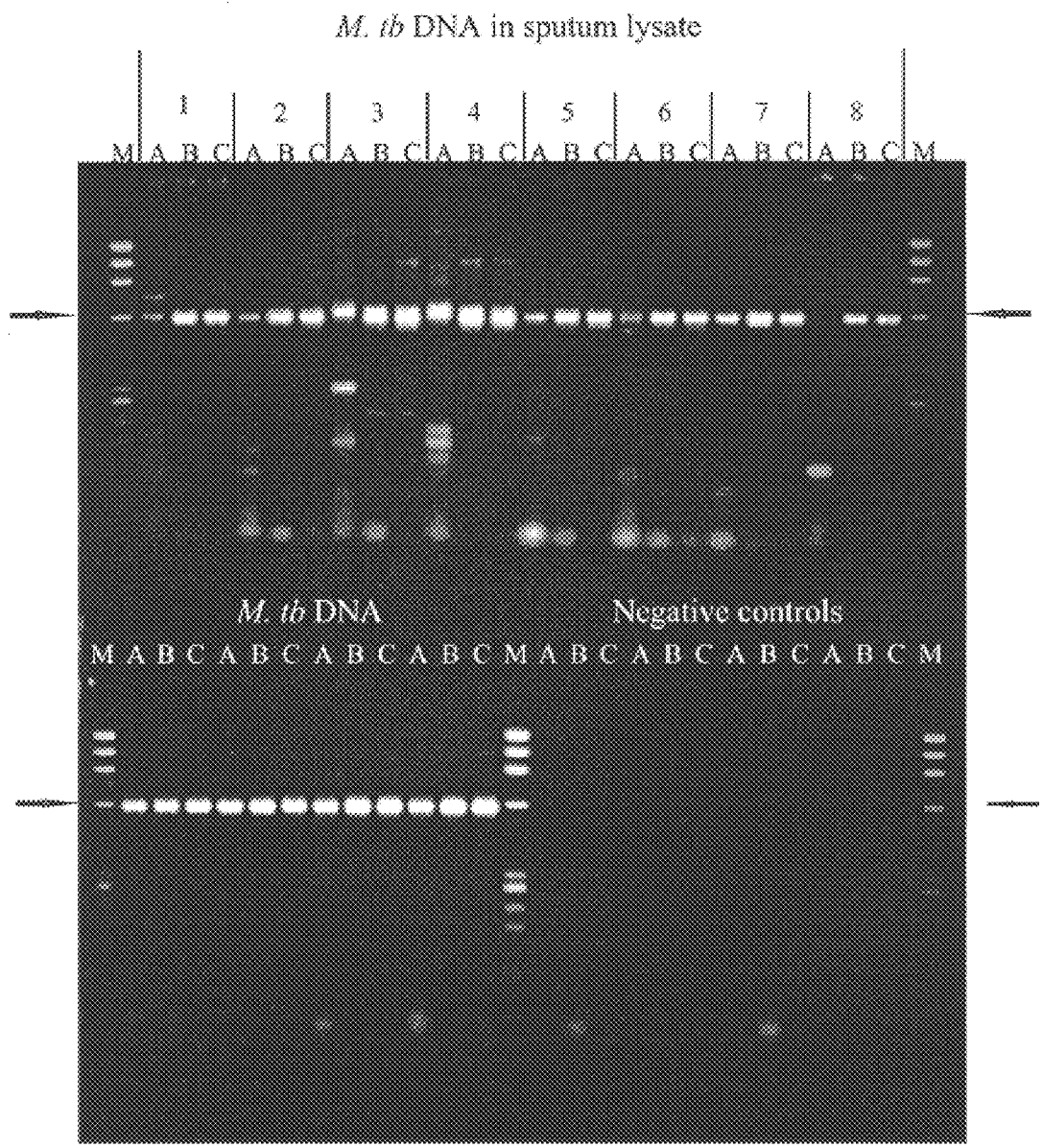
FIG. 5 shows the results of amplifications of mycobacterial DNA using primers modified with a benzyl group and primers modified with a p-tert-butylbenzyl group, as described in Example 10.

The results of the electrophoretic analysis are shown in FIG. 5. For each sample, the products from amplifications carried out with unmodified primers (indicated "A") and with modified primers (indicated "B" and "C") were run on adjacent lanes. The bands corresponding to the intended mycobacterial target sequence are indicated with arrows. Other bands correspond to non-specific amplification product; the lowest bands in the gel correspond to primer dimer. Lanes marked "M" contain a molecular weight marker (Hae III digestion of PhiX174 DNA).

Using the unmodified primers, amplifications of purified mycobacterial DNA resulted in the formation of primer dimer. The use of the either modified primer pairs increased the amount of intended target present and essentially eliminated the formation of detectable primer dimer.

In contrast to amplifications of purified DNA, using the unmodified primers, the presence of sputum lysate in the amplification reaction reduced the efficiency and increased the formation of non-specific amplification product, as shown by the presence of extraneous product bands. The increase of non-specific amplification product is not surprising given that sputum lysates contain a significant amount of human DNA, which was not present in the amplifications of purified mycobacterial DNA. The use of the either of the modified primer pairs in amplifications carried out in the presence of sputum resulted in both a significant increase in the amount of intended product generated and a reduction of non-specific amplification.

EXAMPLE 11

Additional Synthesis of Primers Modified with a Benzyl Group

Primers modified by the addition of a benzyl group to a terminal cytosine were synthesized essentially as described in Example 1, but using an LCAA-CPG-linked $N^4$-acetyl, $N^4$-benzyl-5'-O-DMT-2'-deoxycytidine prepared as described below.

Step 1: Synthesis of $N^4$-benzyl-2'-deoxycytidine

To 2'-deoxycytidine hydrochloride (5.28g, 20 mmol, U.S. Biochemical Corp., Cleveland, Ohio) was added benzylamine (20 ml), and the mixture was heated at 150° C. for 3 hours under an argon atmosphere. The solution was concentrated under vacuum to yield a viscous yellow oil, which was partitioned between water (100 ml) and ethyl acetate (100 ml). The aqueous phase was washed with ethyl acetate (100 ml) and separated. The aqueous phase was concentrated under vacuum to yield a yellow syrup (13 g), which was purified by silica gel column chromatography with 15:1 methylene chloride:methanol as eluant, to yield the desired product (5.8 g, 91.5%), as a colorless syrup.

Step 2: Synthesis of $N^4$-acetyl, $N^4$-benzyl-2'-deoxycytidine $N^4$-benzyl-2'-deoxycytidine (2.5g, 7.9 mmol) was dissolved in 15 ml dry dimethylformamide (15 ml), acetic anhydride (8g, 79 mmol, 10 eq.) was added, and the mixture was stirred overnight at room temperature. The solvent and excess acetic anhydride were evaporated under vacuum. The product was purified by column chromatography with silica gel using 20:1 methylene chloride:methanol as eluant, to yield the title compound (1.3 g, 48%). The compound was highly hygroscopic and was stored desiccated at −20° C.

Step 3: Synthesis of $N^4$-acetyl, $N^4$-benzyl, 5'-O-DMT-2'-deoxycytidine.

$N^4$-acetyl, $N^4$-benzyl-2'-deoxycytidine (76 mg, 0.2 mmol) was dissolved in 1 ml dry pyridine, and DMT-Cl (122 mg, 0.2 mmol, 1.0 eq) was added. The reaction mixture was stirred for 3 hours. Analysis by TLC showed some starting material was left, so a further aliquot of DMT-Cl (61 mg, 0.5 eq) was added and the resulting mixture was stirred for another hour, at which time analysis by TLC showed that the reaction was complete. The reaction was quenched with 15 ml brine solution and the aqueous phase was extracted with methylene chloride (3×15 ml). The combined organic layer was washed with brine (2×15 ml) and dried over anhydrous magnesium sulfate. The solvent was evaporated and the mixture was purified by silica gel chromatography using 50:1 methylene chloride: methanol, to yield $N^4$-acetyl, $N^4$-benzyl, 5'-O-DMT-2'-deoxycytidine (96 mg, 65% yield).

Step 4: Succinylation $N^4$-acetyl, $N^4$-benzyl, 5'-O-DMT-2'-deoxycytidine (96 mg, 0.13 mmol) was dissolved in 2 ml dry pyridine. Succinic anhydride (100 mg, 1.0 mmol) and dimethylaminopyridine (20 mg) were added, and the resulting mixture was stirred at room temperature for three days. The solvent was evaporated and the residue was co-evaporated with toluene (3×10 ml). Chloroform (50 ml) was added to dissolve the residue (sonication was used to help the dissolution). The chloroform layer was washed with brine (3×15 ml), and water (1×15 ml). The organic layer was dried with anhydrous magnesium sulfate. The solvent evaporated to give 108 mg pure $N^4$-acetyl, $N^4$-benzyl, 5'-O-DMT-2'-deoxycytidine-3'-O-succinate (97% yield).

Step 5: Preparation of LCAA-CPG linked 5'-O-DMT-$N^4$-acetyl, $N^4$-benzyl-2'-deoxycytidine-3'-O-succinate Activated CPG was prepared as follows. LCAA-CPG (1.0 g, LCA00500C, CPG Inc., Fairfield, N.J.) was treated with trichloroacetic acid in methylene chloride (3%, 10 ml) and was mixed by rotation on a rotary evaporator (rotovapor, Buchi, Flawil, Switzerland) (no vacuum) for 4 hours. The solvent was filtered off and the CPG was washed with 9:1 triethylamine:ethyldiisopropylamine (3×5 ml), methylene chloride (3×10 ml), and ether (3×10 ml) consecutively, then dried under vacuum.

Coupling of the modified nucleoside intermediate to the acid washed CPG was carried out as follows. To 1 gram activated LCAA-CPG was added $N^4$-acetyl, $N^4$-benzyl, 5'-O-DMT-2'-deoxycytidine, 3'-O-succinate (108 mg, 0.13 mmol), prepared as described above, dimethylaminopyridine (20 mg), and 5 ml dry pyridine. The reaction mixture was rotated on a rotavapor (no vacuum) for three days. The supernatant was filtered off, and the coupled LCAA-CPG was washed sequentially with pyridine (3×5 ml), methylene chloride (3×10 ml), and ether (3×10 ml), and then dried in vacuum.

Capping of the LCAA-CPG linked with $N^4$-acetyl, $N^4$-benzyl, 5'-O-DMT-2'-deoxycytidine-3'-O-succinate was carried out as follows. To the derivatized CPG was added Capping mix reagent A (THF/Lutidine/$Ac_2O$ 8:1: 1, Glen Research DNA synthesis reagents, Sterling, Va.) and B (10% N-methylimidazole in THF, Glen Research), and the reaction mixture was rotated on a rotavapor (no vacuum) overnight. The solution was filtered off, and the coupled LCAA-CPG was washed sequentially with pyridine (3×5 ml), methylene chloride (3×10 ml), THF (3×10 ml), and ether (3×10 ml), and then dried under vacuum.

The coupling capacity of the derivatized LCAA-CPG was determined by treating 5 mg of the product with 3% trichloroacetic acid in methylene chloride, and the amount of the released dimethoxyltrityl carbonium ion was measured by UV spectroscopy. The amount of nucleoside derivative linked to LCAA-CPG was determined to be 19.5 μmol/g.

We claim:

1. An oligonucleotide primer for the amplification of a nucleic acid sequence, said primer having the general structure:

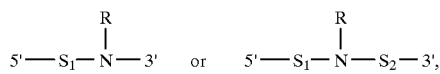

wherein $S_1$ represents a first sequence of nucleotides between about 5 and about 50 nucleotides in length;

wherein $S_2$ represents a second sequence between one and three nucleotides in length;

wherein N represents a nucleotide that contains a purine or pyrimidine base that contains an exocyclic amine;

wherein R represents a modifier group, wherein R is covalently bound to the nitrogen atom of the exocyclic amine, and wherein R has the structure:

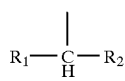

wherein $R_1$ and $R_2$ represent independently hydrogen, a $C_1$–$C_{10}$ alkyl group, an alkoxy group, a phenyl group, a phenoxy group, a substituted phenyl group, a napthyl group, or a substituted napthyl group.

2. An oligonucleotide primer of claim 1, wherein R is a 2-napthylmethyl group; a benzyl group; or a substituted benzyl group.

3. An oligonucleotide primer of claim 2, wherein R is a substituted benzyl group having structure:

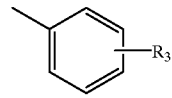

wherein $R_3$ represent a $C_1$–$C_6$ branched or unbranched alkyl group, a methoxy group, or a nitro group.

4. An oligonucleotide primer of claim 3, wherein $R_3$ represent a $C_1$–$C_4$ branched or unbranched alkyl group, a methoxy group, or a nitro group.

5. A primer of claim 4, wherein $R_3$ is attached in the para position.

6. A primer of claim 4, wherein N is adenosine.

7. A primer of claim 6, wherein R is selected from the group consisting of benzyl, p-methylbenzyl, p-tert-butylbenzyl, p-methoxybenzyl, o-nitrobenzyl, and 2-napthylmethyl.

8. A kit for carrying out a nucleic acid amplification reaction, wherein said kit comprises an oligonucleotide primer of claim 1.

9. A kit for carrying out a nucleic acid amplification reaction, wherein said kit comprises an oligonucleotide primer of claim 2.

10. A kit for carrying out a nucleic acid amplification reaction, wherein said kit comprises an oligonucleotide primer of claim 3.

11. A kit for carrying out a nucleic acid amplification reaction, wherein said kit comprises an oligonucleotide primer of claim 4.

12. A kit for carrying out a nucleic acid amplification reaction, wherein said kit comprises an oligonucleotide primer of claim 5.

13. A kit for carrying out a nucleic acid amplification reaction, wherein said kit comprises an oligonucleotide primer of claim 6.

14. A kit for carrying out a nucleic acid amplification reaction, wherein said kit comprises an oligonucleotide primer of claim 7.

15. A method for amplifying a nucleic acid target sequence, wherein said method comprises carrying out an amplification reaction using oligonucleotide primers, wherein at least one primer has the structure:

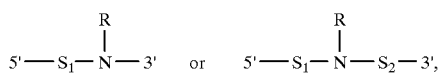

wherein $S_1$ represents a first sequence of nucleotides between about 5 and about 50 nucleotides in length;

wherein $S_2$ represents a second sequence between one and three nucleotides in length;

wherein N represents a nucleotide that contains a purine or pyrimidine base that contains an exocyclic amine;

wherein R represents a modifier group, wherein R is covalently bound to the nitrogen atom of the exocyclic amine, and wherein R has the structure:

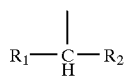

wherein $R_1$ and $R_2$ represent independently hydrogen, a $C_1$–$C_{10}$ alkyl group, an alkoxy group, phenyl group, a phenoxy group, a substituted phenyl group, a napthyl group, or a substituted napthyl group.

16. A method of claim 15, wherein R is a 2-napthylmethyl group; a benzyl group; or a substituted benzyl group.

17. A method of claim 16, wherein R is a substituted benzyl group having structure:

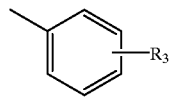

wherein $R_3$ represent a $C_1$14 $C_6$ branched or unbranched alkyl group, more preferably a $C_1$–$C_4$ branched or unbranched alkyl group, a methoxy group, or a nitro group.

18. A method of claim 17, wherein $R_3$ represent a $C_1$–$C_4$ branched or unbranched alkyl group, a methoxy group, or a nitro group.

19. A method of claim 18, wherein $R_3$ is attached in the para position.

20. A method of claim 18, wherein N is adenosine.

21. A method of claim 20, wherein R is selected from the group consisting of benzyl, p-methylbenzyl, p-tert-butylbenzyl, p-methoxybenzyl, o-nitrobenzyl, and 2-napthylmethyl.

22. A method of claim 15, wherein said amplification reaction is a polymerase chain reaction.

* * * * *